United States Patent
Maderna et al.

(10) Patent No.: US 8,884,058 B2
(45) Date of Patent: Nov. 11, 2014

(54) PREPARATION OF (R)-N-(3,4-DIFLUORO-2-(2-FLUORO-4-IODOPHENYLAMINO)-6-METHOXY PHENYL)-1-(2,3-DIHYDROXYPROPYL) CYCLOPROPANE-1-SULFONAMIDE AND (S)-N-(3,4-DIFLUORO-2-(2-FLUORO-4-IODOPHENYLAMINO)-6-METHOXYPHENYL)-1-(2,3-DIHYDROXYPROPYL)CYCLOPROPANE-1-SULFONAMIDE

(71) Applicant: Ardea Biosciences, Inc., San Diego, CA (US)

(72) Inventors: Andreas Maderna, Stony Point, NY (US); Jean Michel Vernier, San Diego, CA (US)

(73) Assignee: Ardea Biosciences, San Diego, CA (US)

( * ) Notice: Subject to any disclaimer, the term of this patent is extended or adjusted under 35 U.S.C. 154(b) by 0 days.

(21) Appl. No.: 13/868,621

(22) Filed: Apr. 23, 2013

(65) Prior Publication Data

US 2013/0261320 A1    Oct. 3, 2013

Related U.S. Application Data

(62) Division of application No. 13/386,519, filed as application No. PCT/EP2010/004222 on Jul. 10, 2010, now Pat. No. 8,513,443.

(60) Provisional application No. 61/228,509, filed on Jul. 24, 2009, provisional application No. 61/228,501, filed on Jul. 24, 2009.

(51) Int. Cl.
    *C07C 303/36*    (2006.01)

(52) U.S. Cl.
    USPC .......................................................... 564/80

(58) Field of Classification Search
    CPC ................................................... C07C 303/36
    USPC .............................................................. 564/80
    See application file for complete search history.

(56) References Cited

U.S. PATENT DOCUMENTS

| | | | |
|---|---|---|---|
| 7,759,518 B2 * | 7/2010 | Maderna et al. | 564/84 |
| 8,101,799 B2 * | 1/2012 | Maderna et al. | 564/84 |
| 8,513,443 B2 * | 8/2013 | Maderna et al. | 549/453 |
| 8,648,116 B2 * | 2/2014 | Vernier et al. | 514/602 |
| 2007/0238710 A1 | 10/2007 | Yan et al. | |
| 2008/0058340 A1 | 3/2008 | Maderna et al. | |

FOREIGN PATENT DOCUMENTS

WO    WO 2007/121269 A2    10/2007

OTHER PUBLICATIONS

International Search Report of PCT/EP2010/004222 (Oct. 15, 2010).

* cited by examiner

*Primary Examiner* — Golam M M Shameem
(74) *Attorney, Agent, or Firm* — Millen, White, Zelano & Branigan, P.C.

(57) ABSTRACT

The present invention relates to the preparation of (R)—N-(3,4-difluoro-2-(2-fluoro-4-iodophenylamino)-6-methoxyphenyl)-1-(2,3-dihydroxypropyl)cyclopropane-1-sulfonamide and (S)—N-(3,4-difluoro-2-(2-fluoro-4-iodophenylamino)-6-methoxyphenyl)-1-(2,3-dihydroxypropyl)cyclopropane-1-sulfonamide.

8 Claims, 3 Drawing Sheets

$^1$H NMR spectrum of sodium (S)-1-((2,2-dimethyl-1,3-dioxolan-4-yl)methyl)cyclopropane-1-sulfonate in CD$_3$OD ppm (δ)

$^{13}$C NMR spectrum of sodium (S)-1-((2,2-dimethyl-1,3-dioxolan-4-yl)methyl)cyclopropane-1-sulfonate in CD$_3$OD ppm (δ)

PREPARATION OF (R)-N-(3,4-DIFLUORO-2-(2-FLUORO-4-IODOPHENYLAMINO)-6-METHOXYPHENYL)-1-(2,3-DIHYDROXYPROPYL)CYCLOPROPANE-1-SULFONAMIDE AND (S)-N-(3,4-DIFLUORO-2-(2-FLUORO-4-IODOPHENYLAMINO)-6-METHOXYPHENYL)-1-(2,3-DIHYDROXYPROPYL)CYCLOPROPANE-1-SULFONAMIDE

BACKGROUND OF THE INVENTION

The present invention relates to the fields of pharmaceutical chemistry and synthetic organic chemistry. (R)—N-(3,4-Difluoro-2-(2-fluoro-4-iodophenylamino)-6-methoxyphenyl)-1-(2,3-dihydroxypropyl)cyclopropane-1-sulfonamide and (S)—N-(3,4-difluoro-2-(2-fluoro-4-iodophenylamino)-6-methoxyphenyl)-1-(2,3-dihydroxypropyl)cyclopropane-1-sulfonamide are known to possess inhibitory properties against MEK enzymes and are of therapeutic value (see US published patent application US 2008/0058340 A1). Described herein are methods for their preparation.

SUMMARY OF THE INVENTION

Provided herein are processes for preparing compounds of formula (I-a):

formula (I-a)

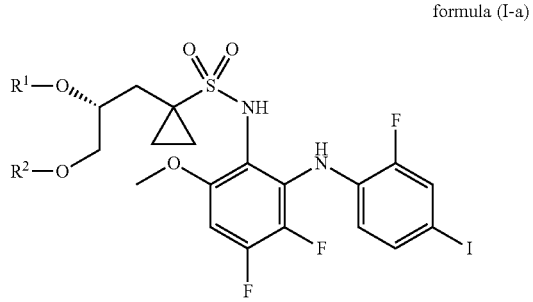

comprising, contacting 5,6-difluoro-$N^1$-(2-fluoro-4-iodophenyl)-3-methoxybenzene-1,2-diamine with a compound of formula (II-a):

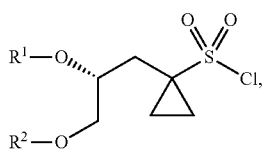

wherein
$R^1$ is H or an alcohol protecting group;
$R^2$ is H or an alcohol protecting group; or
$R^1$ and $R^2$ together with the carbon atoms to which they are attached form a cyclic 1,2-diol protecting group.

In some embodiments, the compound of formula (I-a) is (R)—N-(3,4-difluoro-2-(2-fluoro-4-iodophenylamino)-6-methoxyphenyl)-1-((2,2-dimethyl-1,3-dioxolan-4-yl)methyl)cyclopropane-1-sulfonamide:

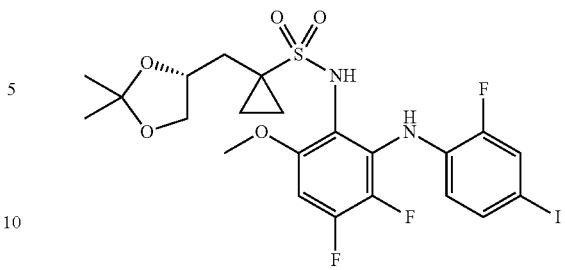

In some embodiments, the compound of formula (II-a) is (R)-1-((2,2-dimethyl-1,3-dioxolan-4-yl)methyl)cyclopropane-1-sulfonyl chloride:

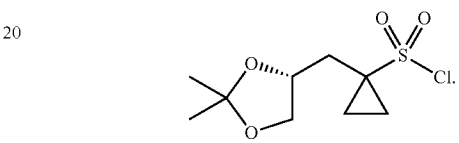

Also provided herein are processes for preparing compounds of formula (I-b):

formula (I-b)

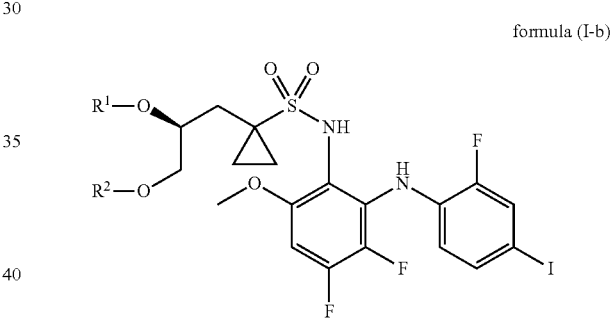

comprising, contacting 5,6-difluoro-$N^1$-(2-fluoro-4-iodophenyl)-3-methoxybenzene-1,2-diamine with a compound of formula (II-b):

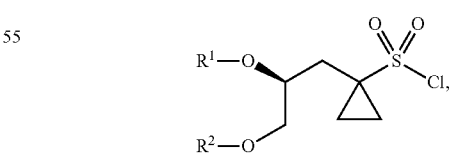

wherein
$R^1$ is H or an alcohol protecting group;
$R^2$ is H or an alcohol protecting group; or
$R^1$ and $R^2$ together with the carbon atoms to which they are attached form a cyclic 1,2-diol protecting group.

In some embodiments, the compound of formula (I-b) is (S)—N-(3,4-difluoro-2-(2-fluoro-4-iodophenylamino)-6-methoxyphenyl)-1-((2,2-dimethyl-1,3-dioxolan-4-yl)methyl)cyclopropane-1-sulfonamide:

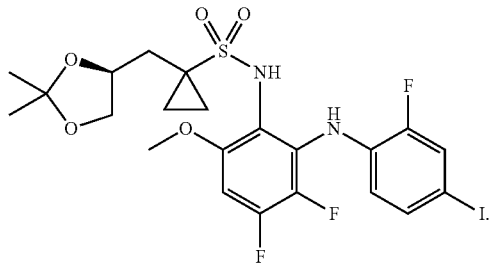 [SMILES: COc1cc(F)c(F)c(Nc2ccc(I)cc2F)c1NS(=O)(=O)C1(C[C@H]2COC(C)(C)O2)CC1]

In some embodiments, the compound of formula (II-b) is (S)-1-((2,2-dimethyl-1,3-dioxolan-4-yl)methyl)cyclopropane-1-sulfonyl chloride:

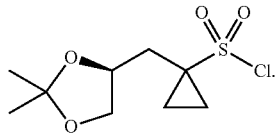

Also provided herein are processes for preparing (R)—N-(3,4-difluoro-2-(2-fluoro-4-iodophenylamino)-6-methoxyphenyl)-1-(2,3-dihydroxypropyl)cyclopropane-1-sulfonamide, comprising, contacting a compound of formula (I-a) with an acid, a base or a nucleophile; or exposing the compound of formula (I-a) to UV light:

formula (I-a)

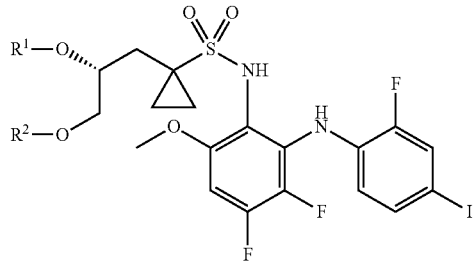

wherein

R¹ is H or an alcohol protecting group;
R² is H or an alcohol protecting group; or
R¹ and R² together with the carbon atoms to which they are attached form a cyclic 1,2-diol protecting group.

In some embodiments, the compound of formula (I-a) is (R)—N-(3,4-difluoro-2-(2-fluoro-4-iodophenylamino)-6-methoxyphenyl)-1-((2,2-dimethyl-1,3-dioxolan-4-yl)methyl)cyclopropane-1-sulfonamide:

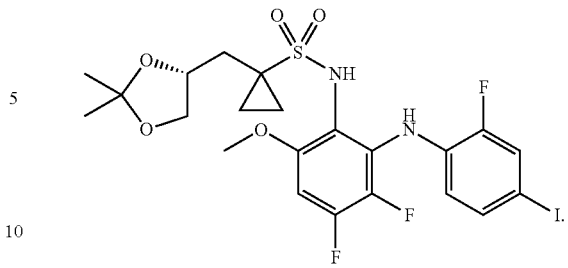

Also provided herein are processes for preparing (S)—N-(3,4-difluoro-2-(2-fluoro-4-iodophenylamino)-6-methoxyphenyl)-1-(2,3-dihydroxypropyl)cyclopropane-1-sulfonamide, comprising, contacting a compound of formula (I-b) with an acid, a base or a nucleophile; or exposing the compound of formula (I-b) to UV light:

formula (I-b)

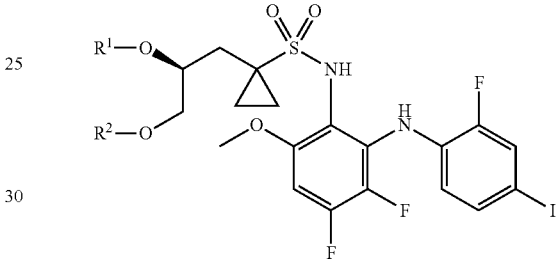

wherein
R¹ is H or an alcohol protecting group;
R² is H or an alcohol protecting group; or
R¹ and R² together with the carbon atoms to which they are attached form a cyclic 1,2-diol protecting group.

In some embodiments, the compound of formula (I-b) is (S)—N-(3,4-difluoro-2-(2-fluoro-4-iodophenylamino)-6-methoxyphenyl)-1-((2,2-dimethyl-1,3-dioxolan-4-yl)methyl)cyclopropane-1-sulfonamide:

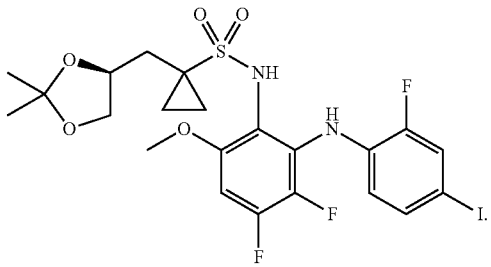 [SMILES: COc1cc(F)c(F)c(Nc2ccc(I)cc2F)c1NS(=O)(=O)C1(C[C@H]2COC(C)(C)O2)CC1]

In some embodiments, R¹ is H and R² is an alcohol protecting group. In further or additional embodiments, R² is H and R¹ is an alcohol protecting group. In further or additional embodiments, both R¹ and R² are alcohol protecting groups. In further or additional embodiments, both R¹ and R² are hydrogen. In further or additional embodiments, the protecting groups are the same. In further or additional embodiments, the protecting groups are different. In further or additional embodiments, R¹ and R² together with the carbon atoms to which they are attached form a cyclic 1,2-diol protecting group. In further or additional embodiments, the cyclic 1,2-diol protecting group is a 5-membered cyclic 1,2-diol protecting group. In further or additional embodiments, the cyclic 1,2-diol protecting group is 2,2-dimethyl-1,3-dioxolan-4-yl.

Also provided herein are compounds useful for the preparation of (R)—N-(3,4-difluoro-2-(2-fluoro-4-iodophenylamino)-6-methoxyphenyl)-1-(2,3-dihydroxypropyl)cyclopropane-1-sulfonamide or (S)—N-(3,4-difluoro-2-(2-fluoro-4-iodophenylamino)-6-methoxyphenyl)-1-(2,3-dihydroxypropyl)cyclopropane-1-sulfonamide.

In some embodiments, the compounds (R)-1-((2,2-dimethyl-1,3-dioxolan-4-yl)methyl)cyclopropane-1-sulfonyl chloride and (S)-1-((2,2-dimethyl-1,3-dioxolan-4-yl)methyl)cyclopropane-1-sulfonyl chloride are provided:

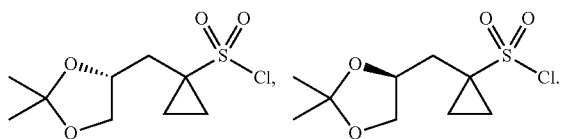

In some embodiments, the compounds (R)-3-(2,2-dimethyl-1,3-dioxolan-4-yl)prop-1-ene-2-sulfonyl chloride and (S)-3-(2,2-dimethyl-1,3-dioxolan-4-yl)prop-1-ene-2-sulfonyl chloride are provided:

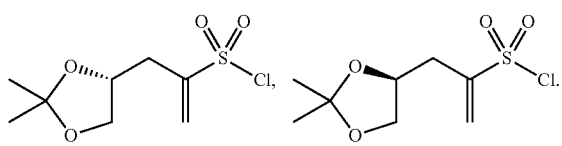

In some embodiments, the compounds sodium (R)-1-((2,2-dimethyl-1,3-dioxolan-4-yl)methyl)cyclopropane-1-sulfonate and sodium (S)-1-((2,2-dimethyl-1,3-dioxolan-4-yl)methyl)cyclopropane-1-sulfonate are provided:

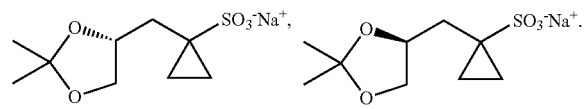

In some embodiments, the compounds (R)-1-((2,2-dimethyl-1,3-dioxolan-4-yl)methyl)cyclopropanethiol and (S)-1-((2,2-dimethyl-1,3-dioxolan-4-yl)methyl)cyclopropanethiol are provided:

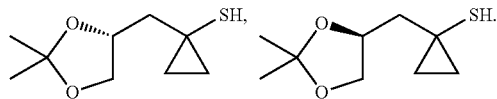

In some embodiments, the compounds 1,2-bis(1-(((R)-2,2-dimethyl-1,3-dioxolan-4-yl)methyl)cyclopropyl)disulfane and 1,2-bis(1-(((S)-2,2-dimethyl-1,3-dioxolan-4-yl)methyl)cyclopropyl)disulfane are provided:

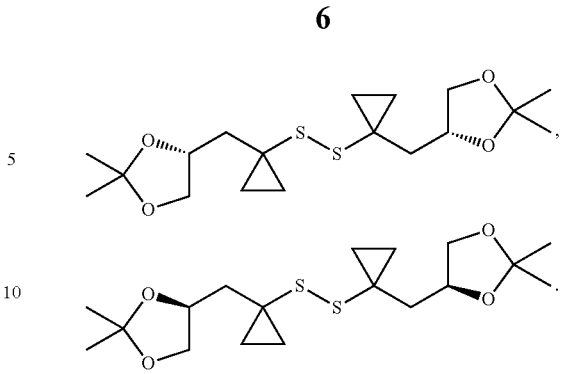

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
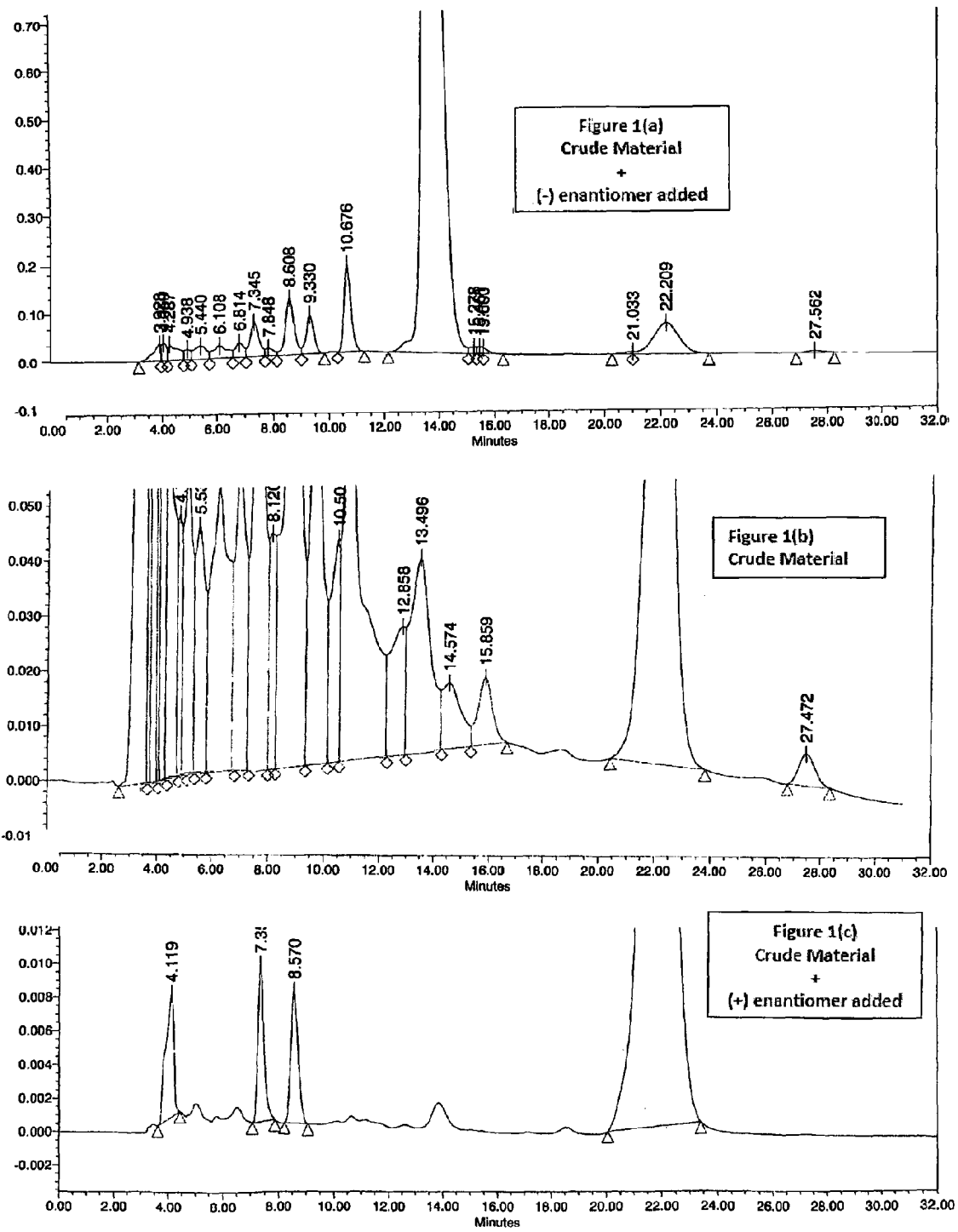
FIG. 1 represents three HPLC traces of N-(3,4-difluoro-2-(2-fluoro-4-iodophenylamino)-6-methoxyphenyl)-1-(2,3-dihydroxypropyl)cyclopropane-1-sulfonamide, wherein the top trace 1(a) is the HPLC trace of the crude material, co-injected with an authentic sample of the (−) enantiomer (obtained via chiral separation of the racemic mixture of both isomers); the middle trace 1(b) is the HPLC trace of the crude material; and the lower trace 1(c) is the HPLC trace of the crude material, co-injected with an authentic sample of the (+) enantiomer (obtained via chiral separation of the racemic mixture of both isomers).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

It is often desirable to have alternate methods for the preparation of useful compounds. Described herein are various methods for the preparation of (R)—N-(3,4-difluoro-2-(2- fluoro-4-iodophenylamino)-6-methoxyphenyl)-1-(2,3-dihy-droxypropyl)cyclopropane-1-sulfonamide and (S)—N-(3,4-difluoro-2-(2-fluoro-4-iodophenylamino)-6-methoxyphenyl)-1-(2,3-dihydroxypropyl)cyclopropane-1-sulfonamide which are known to possess inhibitory properties against MEK enzymes.

I. Preparation of Compounds

Method of Chemical Synthesis

The discussion below is offered to illustrate how, in principle, to gain access to the compounds claimed under this invention and to give details on certain of the diverse methods available for use in assembling the compounds of the invention. However, the discussion is not intended to define or limit the scope of reactions or reaction sequences that are useful in preparing the compounds of the present invention. The compounds of this invention may be made by the procedures and techniques disclosed in the Examples section below, as well as by known organic synthesis techniques.

Methods known to a practitioner of ordinary skill in the art may be identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Specific and analogous reactants may also be identified through the indices of known chemicals prepared by the Chemical Abstract Service of the American Chemical Society, which are available in most public and university libraries, as well as through on-line databases. Chemicals that are known but not commercially available in catalogs may be prepared by custom chemical synthesis houses, where many of the standard chemical supply houses (e.g., those listed above) provide custom synthesis services.

Method A:

Achiral Synthesis, Followed by Chiral Separation

The achiral synthesis of N-(3,4-difluoro-2-(2-fluoro-4-iodophenylamino)-6-methoxyphenyl)-1-(2,3-dihydroxypropyl)cyclopropane-1-sulfonamide has been described previously, (see US published patent application US 2008/0058340 A1), and is summarized below in scheme 1. The product is obtained as a racemic mixture of the (R) and (S) enantiomers, which are separated via chiral HPLC.

Scheme 1: Achiral synthesis of N-(3,4-difluoro-2-(2-fluoro-4-iodophenylamino)-6-methoxyphenyl)-1-(2,3-dihydroxypropyl)cyclopropane-1-sulfonamide

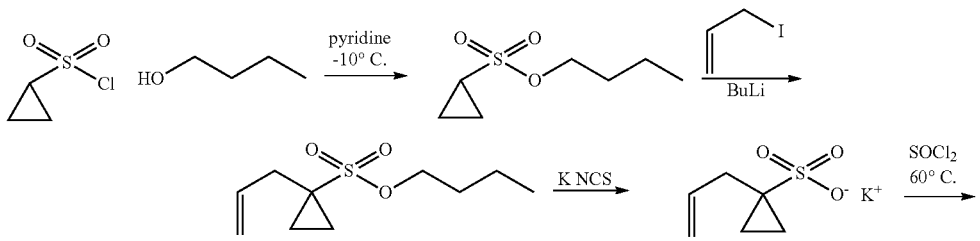

-continued

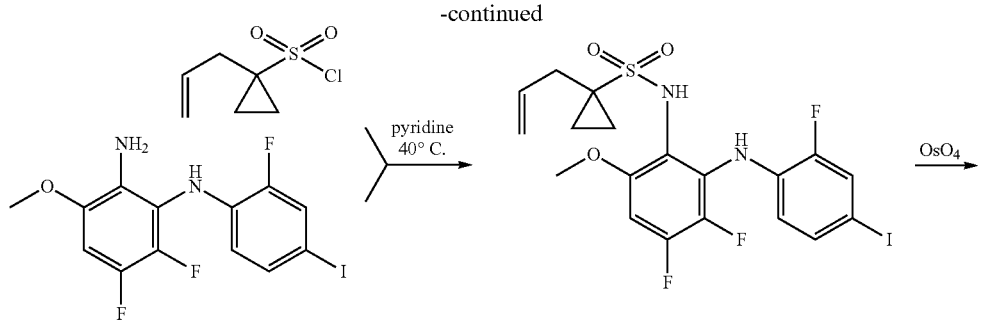

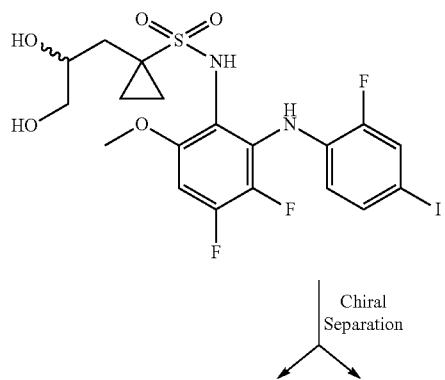

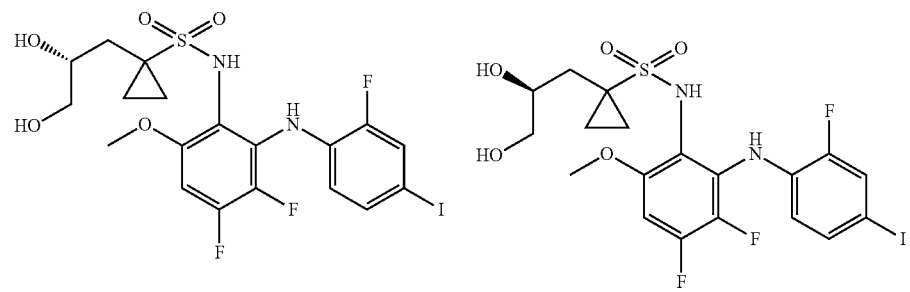

Method B:
Synthesis from Chiral Starting Materials

Schemes 2a, 3a, 4a, 5a and 6a show synthetic routes by which (R)—N-(3,4-difluoro-2-(2-fluoro-4-iodophenylamino)-6-methoxyphenyl)-1-(2,3-dihydroxypropyl)cyclopropane-1-sulfonamide could be prepared, and are discussed below.

Schemes 2b, 3b, 4b, 5b and 6b show synthetic routes by which (S)—N-(3,4-difluoro-2-(2-fluoro-4-iodophenylamino)-6-methoxyphenyl)-1-(2,3-dihydroxypropyl)cyclopropane-1-sulfonamide could be prepared, and are discussed below.

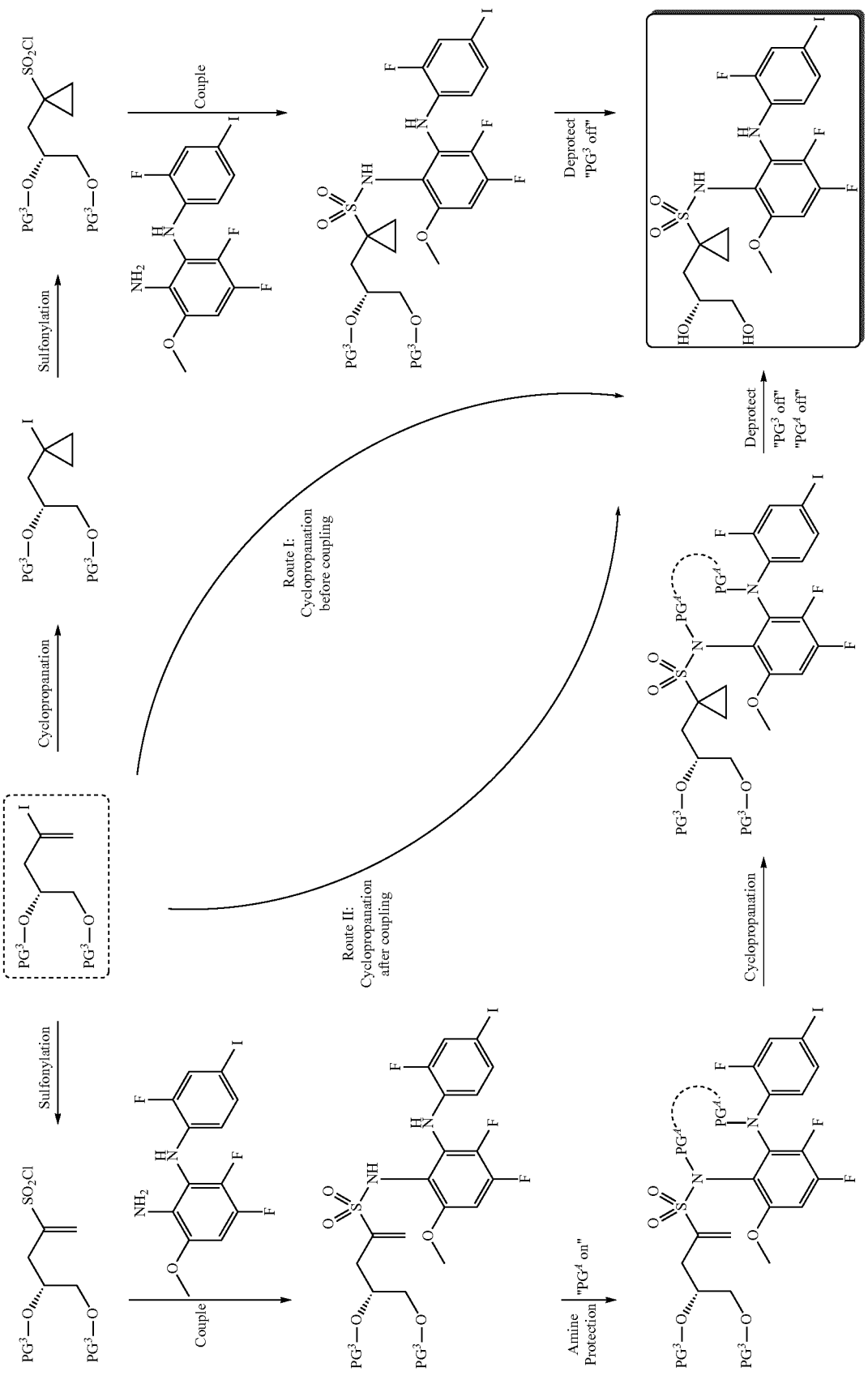

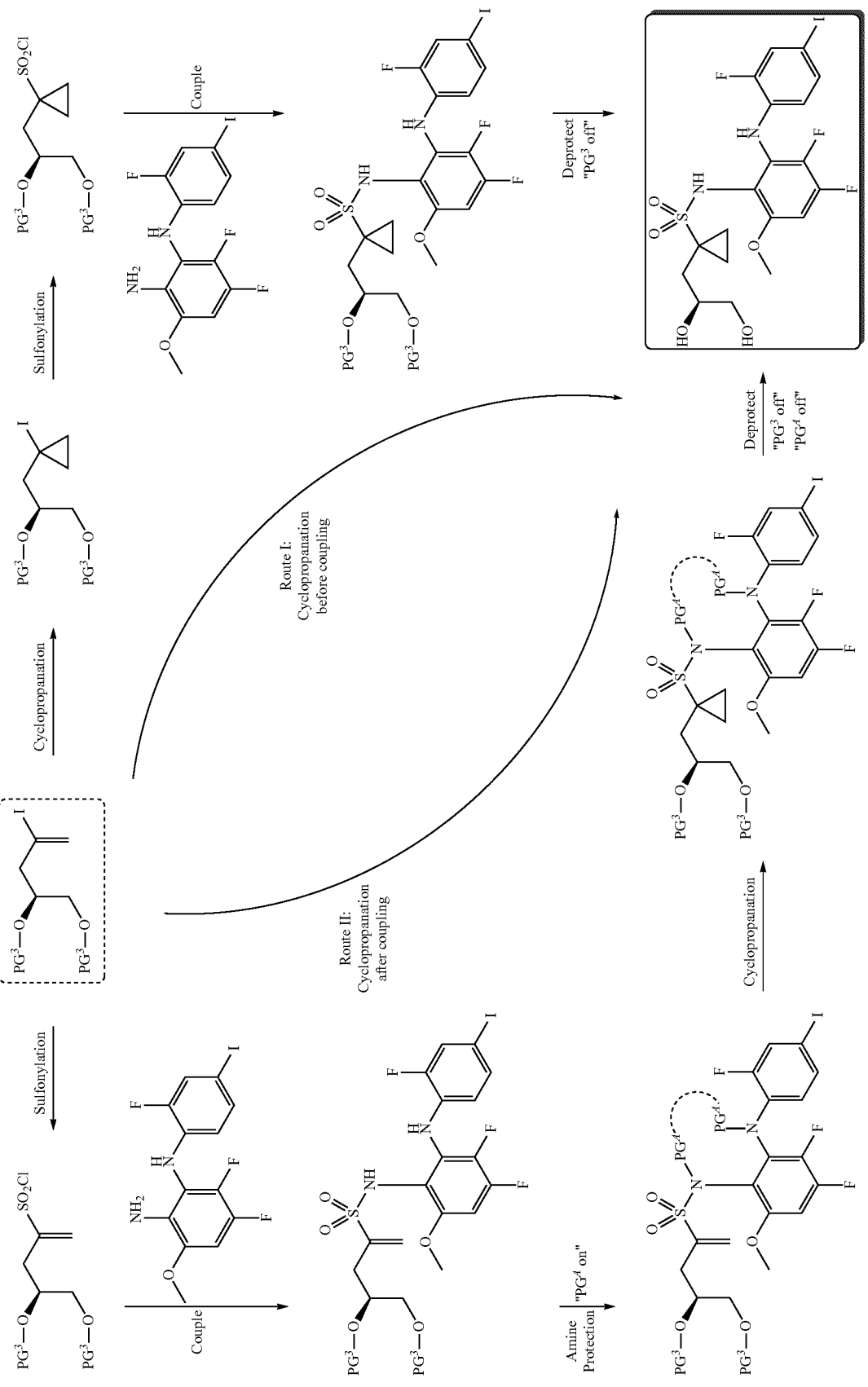
Scheme 2b: (S)-N-(3,4-difluoro-2-(2-fluoro-4-iodophenylamino)-6-methoxyphenyl)-1-(2,3-dihydroxypropyl)cyclopropane-1-sulfonamide Method B, Route I:

A cyclopropyl group is introduced across the alkene of diol-protected 4-iodopent-4-ene-1,2-diol, to form the protected 3-(1-iodocyclopropyl)propane-1,2-diol derivative, which is then sulfonylated. Coupling with 5,6-difluoro-N[1]-(2-fluoro-4-iodophenyl)-3-methoxybenzene-1,2-diamine and final deprotection yields (R)—N-(3,4-difluoro-2-(2-fluoro-4-iodophenylamino)-6-methoxyphenyl)-1-(2,3-dihydroxypropyl)cyclopropane-1-sulfonamide, (S)—N-(3,4-difluoro-2-(2-fluoro-4-iodophenylamino)-6-methoxyphenyl)-1-(2,3-dihydroxypropyl)cyclopropane-1-sulfonamide or the racemic mixture, depending on the starting material employed.

Method B, Route II:

In a slightly different approach to route A above, the cyclopropanation reaction may be affected after coupling with the diaryl amine. Diol protected 4-iodopent-4-ene-1,2-diol is converted to the sulfonyl chloride and then coupled with 5,6-difluoro-N[1]-(2-fluoro-4-iodophenyl)-3-methoxybenzene-1,2-diamine. The amine functionalities are protected, as necessary, the alkene converted to the cyclopropyl group and finally any remaining protecting groups removed as required to yield (R)—N-(3,4-difluoro-2-(2-fluoro-4-iodophenylamino)-6-methoxyphenyl)-1-(2,3-dihydroxypropyl)cyclopropane-1-sulfonamide, (S)—N-(3,4-difluoro-2-(2-fluoro-4-iodophenylamino)-6-methoxyphenyl)-1-(2,3-dihydroxypropyl)cyclopropane-1-sulfonamide or the racemic mixture, depending on the starting material employed.

Both of these routes require as starting material, a diol-protected 4-iodopent-4-ene-1,2-diol, which may be prepared according to the following scheme:

Scheme 3a: (R)-diol-protected 4-iodopent-4-ene-1,2-diol

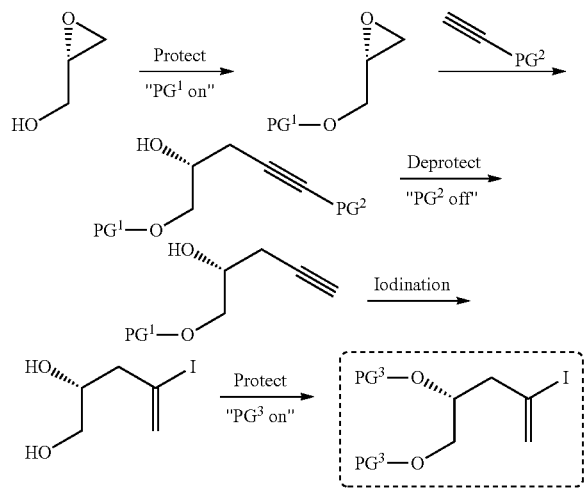

Scheme 3b: (S)-diol-protected 4-iodopent-4-ene-1,2-diol

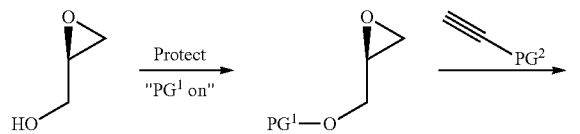

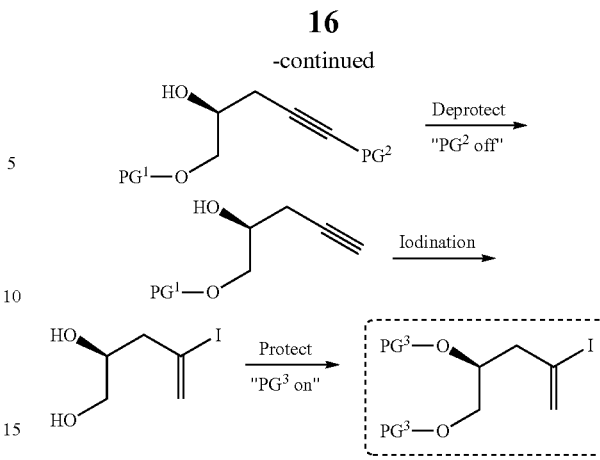

Starting material, glycidol is available commercially as the (R) enantiomer, the (S) enantiomer or the (R/S)-(+/−)-mixture. The alcohol can be protected, for example by reaction with 'butyldimethylsilyl chloride, or other suitable protecting group. Alternatively, the TBS protected glycidol is available commercially as the (R) enantiomer, the (S) enantiomer or the (R/S)-(+/−)-racemic mixture. Coupling with a protected acetylene, followed by deprotection and iodination with a reagent such as 9-iodo-9-borabicyclo[3.3.1]nonane (9-I-BBN), provides 4-iodopent-4-ene-1,2-diol, which is then diol-protected. Note that although there is no inversion of stereochemistry during this synthesis, starting with (R)-(+)-glycidol will result in the formation of (S)—N-(3,4-difluoro-2-(2-fluoro-4-iodophenylamino)-6-methoxyphenyl)-1-(2,3-dihydroxypropyl)cyclopropane-1-sulfonamide; starting with (S)-(−)-glycidol will result in the formation of (R)—N-(3,4-difluoro-2-(2-fluoro-4-iodophenylamino)-6-methoxyphenyl)-1-(2,3-dihydroxypropyl)cyclopropane-1-sulfonamide.

Method B, Diol protected 1-(2,3-dihydroxypropyl)cyclopropane-1-sulfonyl chloride:

In some embodiments, the diol protected 1-(2,3-dihydroxypropyl)cyclopropane-1-sulfonyl chloride intermediate is used. 1,2 Diol protecting groups are well known in the art such as, though not limited to 1,3-dioxolane, 2-methyl-1,3-dioxolane, 2,2-dimethyl-1,3-dioxolane, 2-'butyl-1,3-dioxolane, 2-phenyl-1,3-dioxolane, 1,4-dioxaspiro[4.5]decane, di-para-methoxybenzyloxymethyl ether, di-'butyldimethylsilyl ether, and the like:

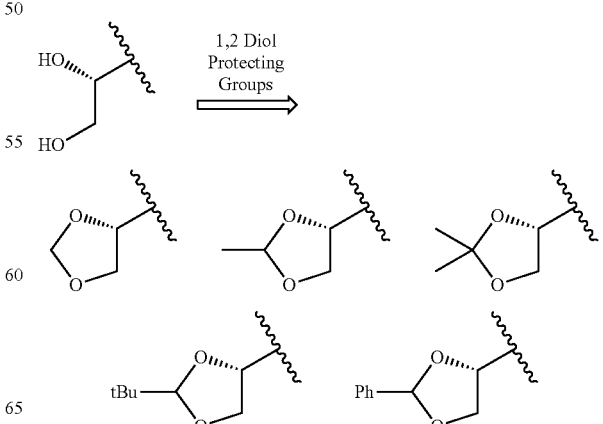

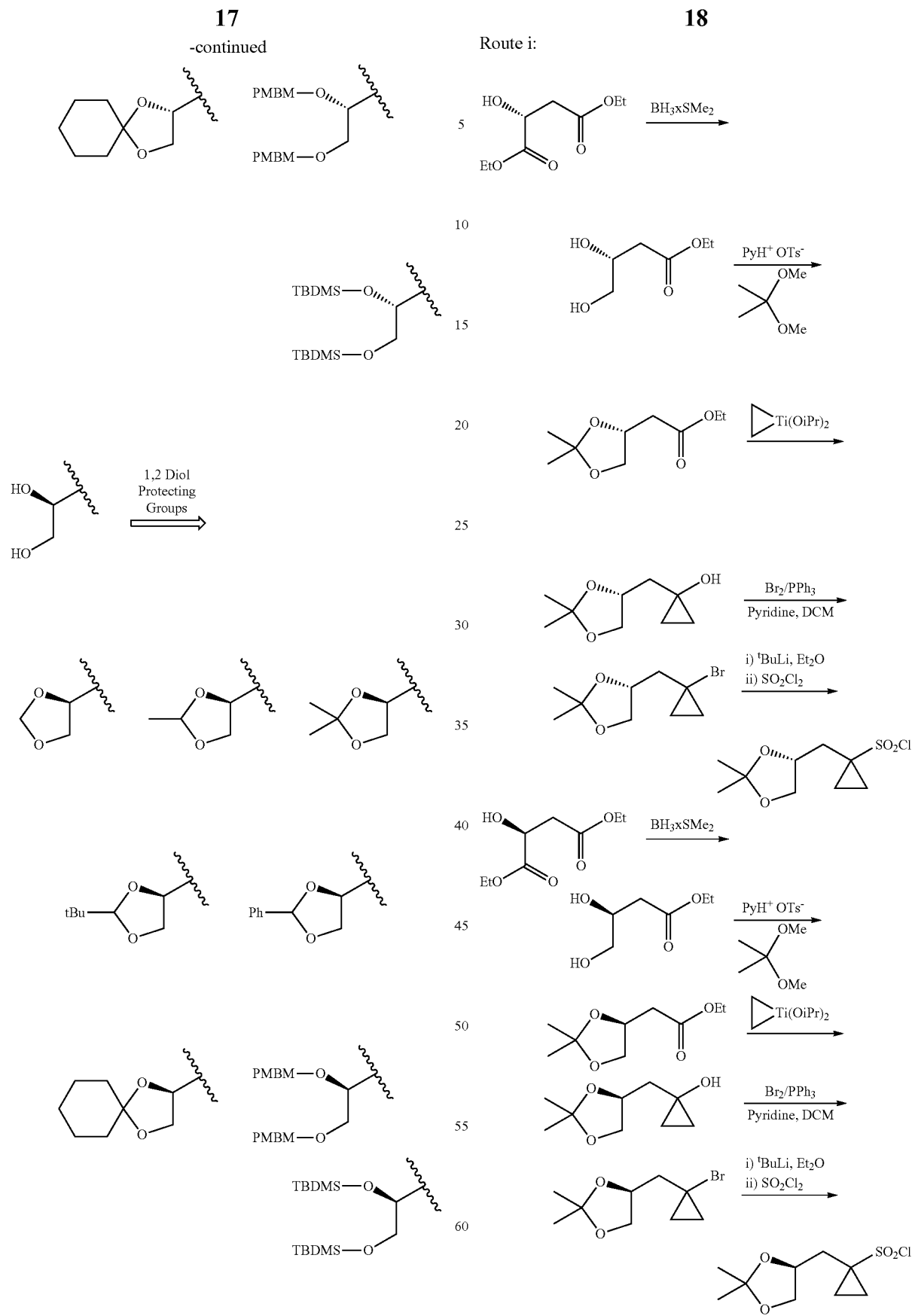
Synthetic schemes for the preparation of 1-((2,2-dimethyl-1,3-dioxolan-4-yl)methyl)cyclopropane-1-sulfonyl chloride are provided below:

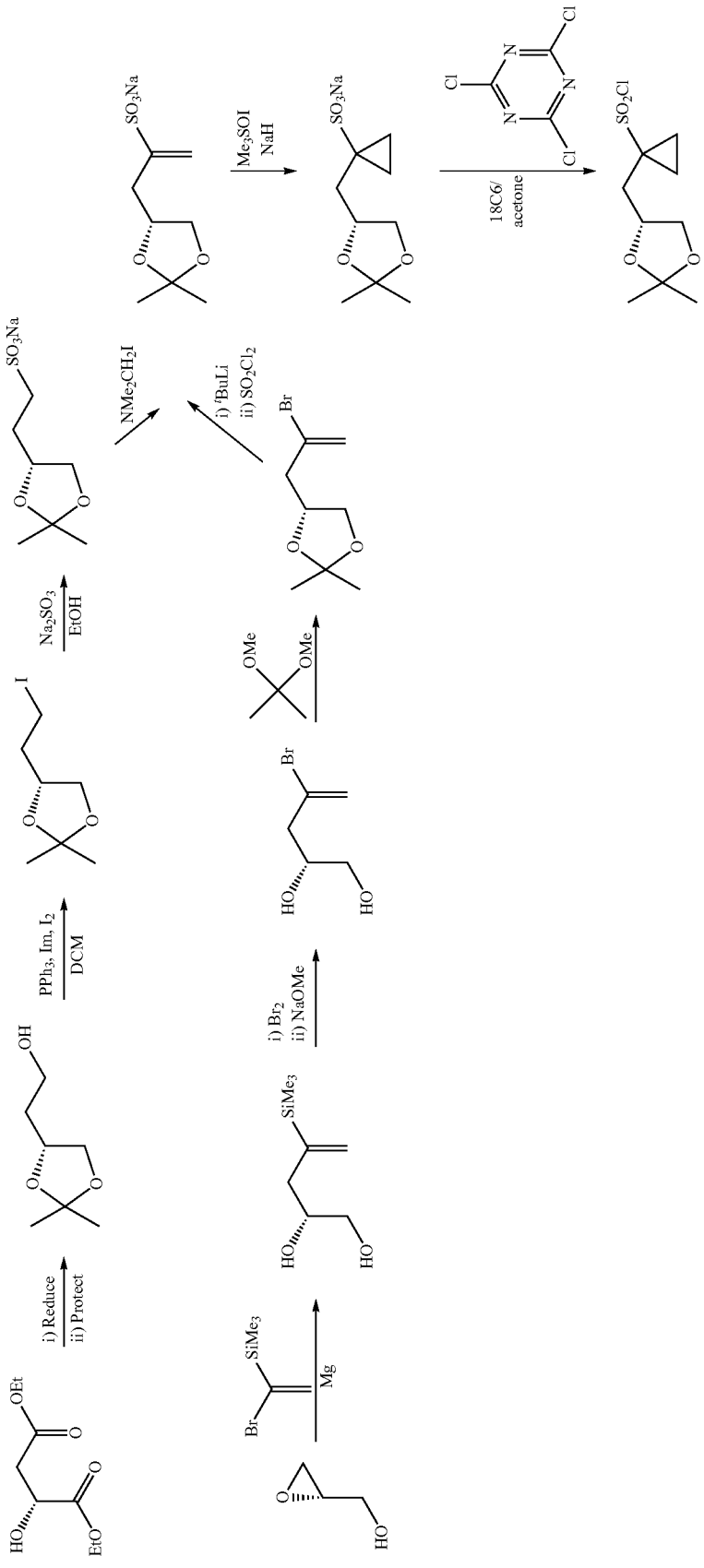

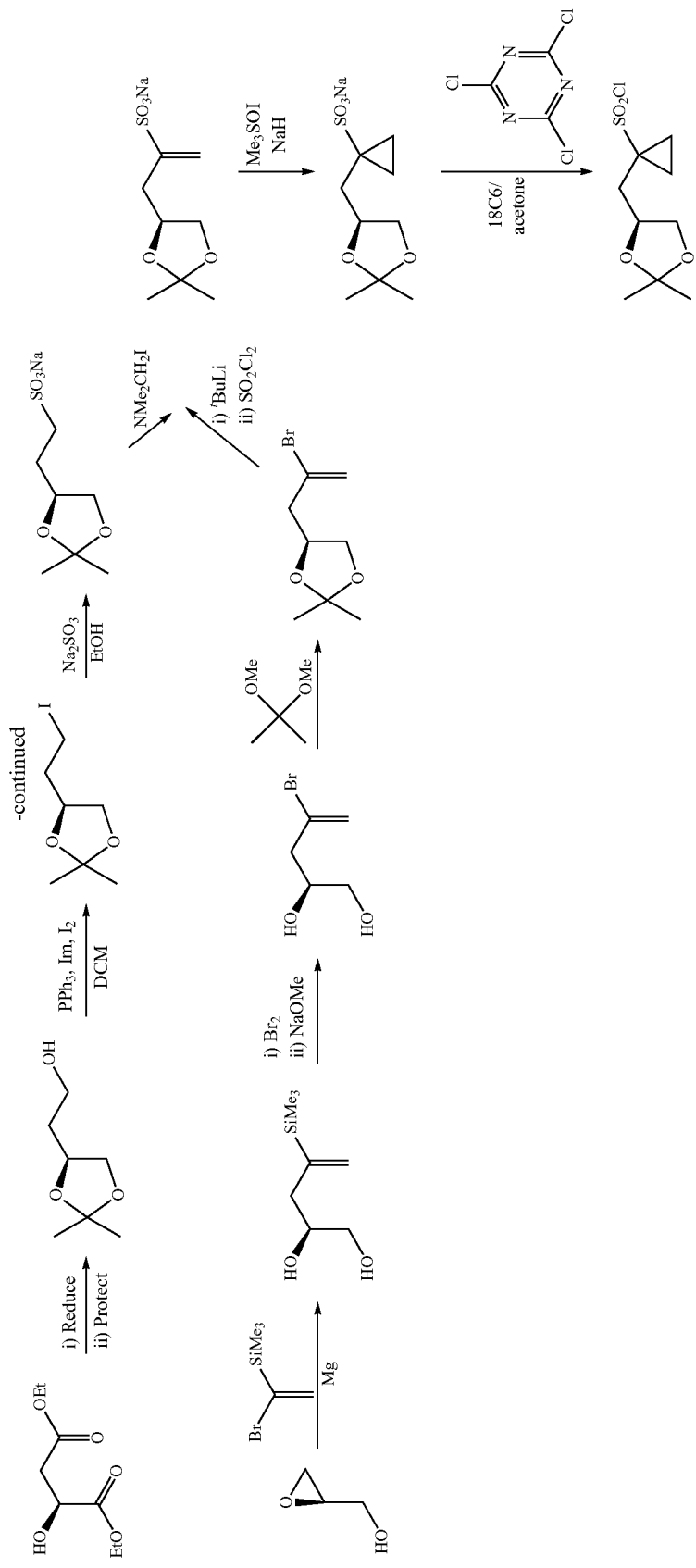

Route iii:

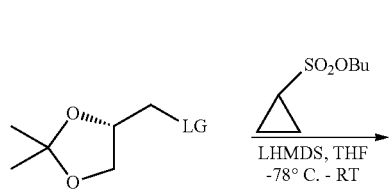

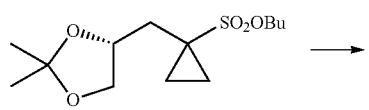

Method B, Route III

Scheme 4a: (R)-N-(3,4-difluoro-2-(2-fluoro-4-iodophenylamino)-6-methoxyphenyl)-1-(2,3-dihydroxypropyl)cyclopropane-1-sulfonamide

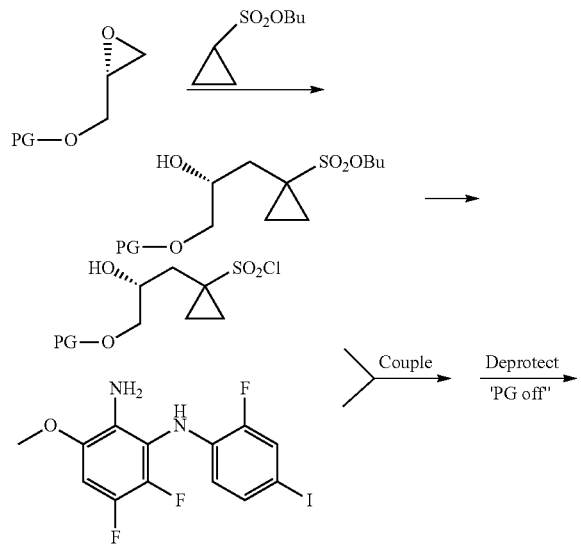

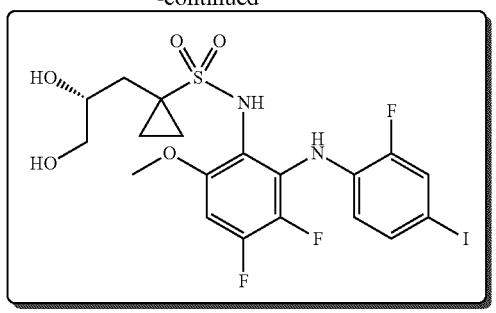

Scheme 4b: (S)-N-(3,4-difluoro-2-(2-fluoro-4-iodophenylamino)-6-methoxyphenyl)-1-(2,3-dihydroxypropyl)cyclopropane-1-sulfonamide

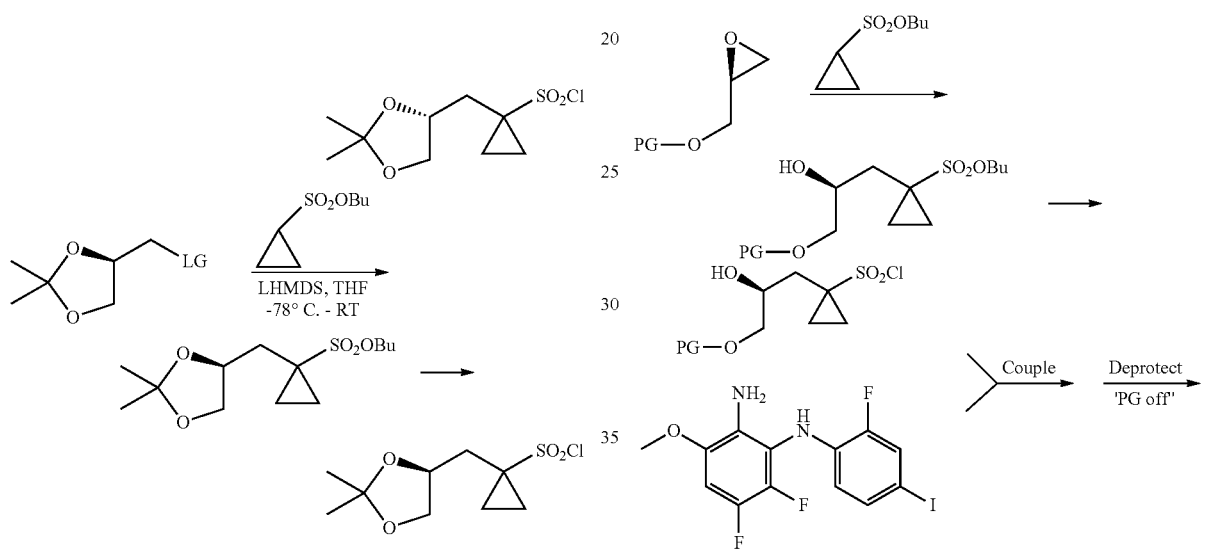

Coupling the protected glycidol with cyclopropanesulfonate ester, such as butyl cyclopropanesulfonate, yields butyl 1-(2-hydroxy-3-protected-hydroxypropyl)cyclopropane-1-sulfonate. Conversion of the sulfonate to the sulfonyl chloride provides the sulfonyl chloride derivative, 1-(2-hydroxy-3-protected-hydroxypropyl)cyclopropane-1-sulfonyl chloride, which is then coupled with 5,6-difluoro-$N^1$-(2-fluoro-4-iodophenyl)-3-methoxybenzene-1,2-diamine. Removal of any residual protecting groups, as required, yields (R)—N-(3,4-difluoro-2-(2-fluoro-4-iodophenylamino)-6-methoxyphenyl)-1-(2,3-dihydroxypropyl)cyclopropane-1-sulfonamide, (S)—N-(3,4-difluoro-2-(2-fluoro-4-iodophenylamino)-6-methoxyphenyl)-1-(2,3-dihydroxypropyl)cyclopropane-1-sulfonamide or the racemic mixture, depending on the starting material employed.

Method B, Route IV

Scheme 5a: (R)-N-(3,4-difluoro-2-(2-fluoro-4-iodophenylamino)-6-methoxyphenyl)-1-(2,3-dihydroxypropyl)cyclopropane-1-sulfonamide

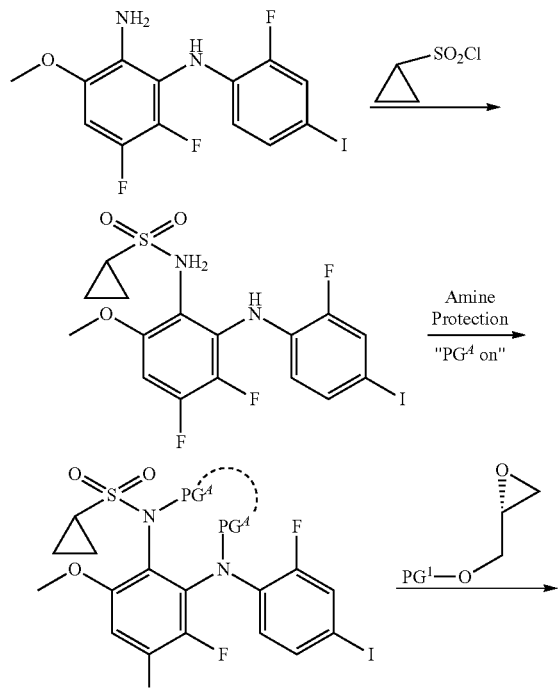

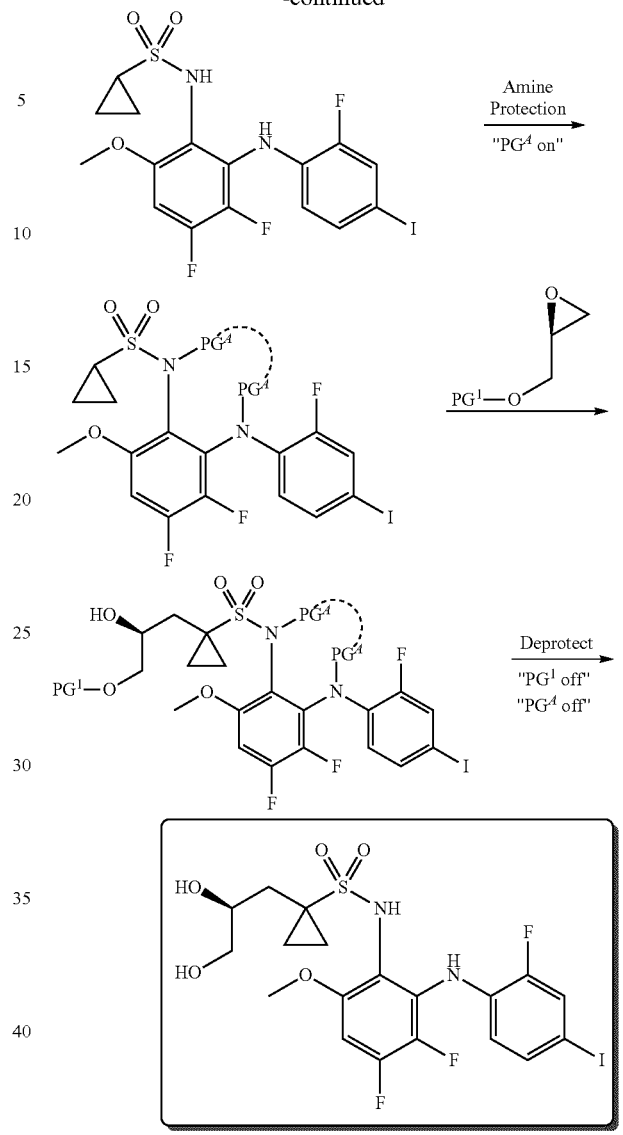

5,6-Difluoro-N[1]-(2-fluoro-4-iodophenyl)-3-methoxybenzene-1,2-diamine is coupled with cyclopropane sulfonyl chloride to provide N-(3,4-difluoro-2-(2-fluoro-4-iodophenylamino)-6-methoxyphenyl)cyclopropanesulfonamide.
The amine groups are protected as required, using suitable protecting groups, such as, but not limited to propyl, dipropyl, para-methoxybenzyl, di-para-methoxybenzyl, cyclic groups, and the like:

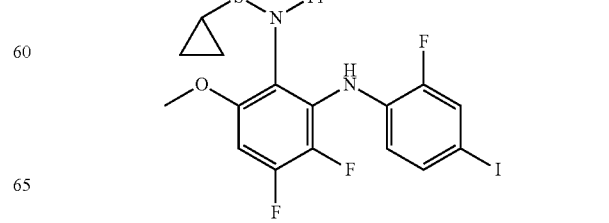

Scheme 5b: (S)-N-(3,4-difluoro-2-(2-fluoro-4-iodophenylamino)-6-methoxyphenyl)-1-(2,3-dihydroxypropyl)cyclopropane-1-sulfonamide

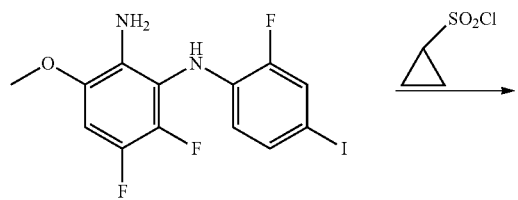

27

-continued

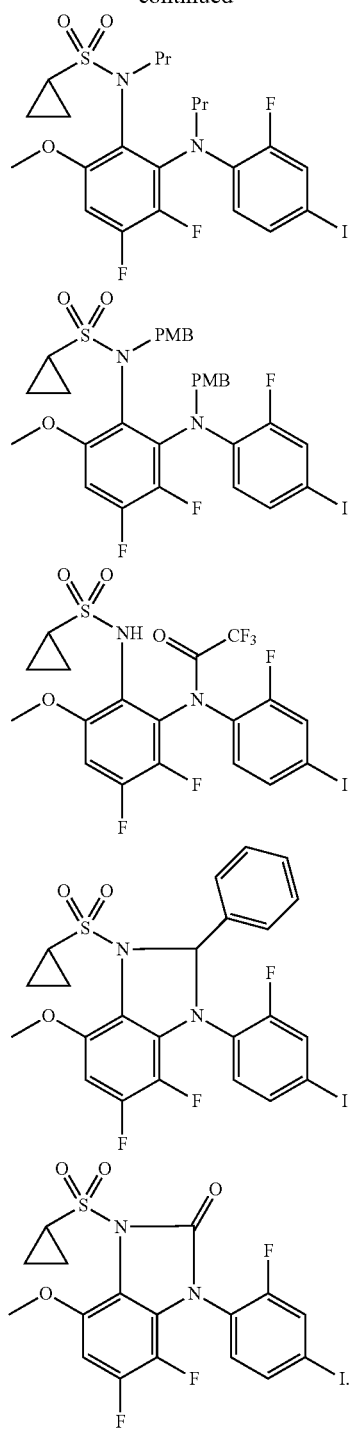

Amine protected N-(3,4-difluoro-2-(2-fluoro-4-iodophenylamino)-6-methoxyphenyl)cyclopropanesulfonamide is coupled with protected glycidol, which after final removal of protecting groups, as required, yields (R)—N-(3,4-difluoro-2-(2-fluoro-4-iodophenylamino)-6-methoxyphenyl)-1-(2,3-dihydroxypropyl)cyclopropane-1-sulfonamide, (S)—N-(3,4-difluoro-2-(2-fluoro-4-iodophenylamino)-6-methoxyphenyl)-1-(2,3-dihydroxypropyl)cyclopropane-1-sulfonamide or the racemic mixture, depending on the glycidol employed.

28

Method B, Route V

Scheme 6a: (R)-N-(3,4-difluoro-2-(2-fluoro-4-iodophenylamino)-6-methoxyphenyl)-1-(2,3-dihydroxypropyl)cyclopropane-1-sulfonamide

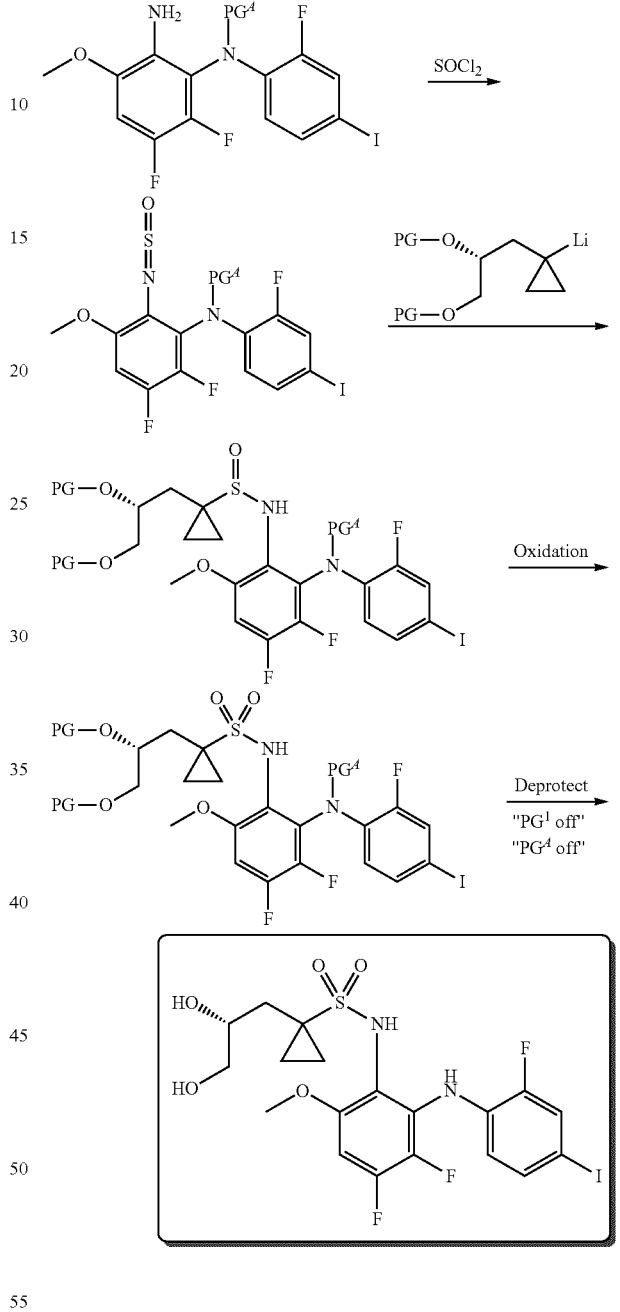

Scheme 6b: (S)-N-(3,4-difluoro-2-(2-fluoro-4-iodophenylamino)-6-methoxyphenyl)-1-(2,3-dihydroxypropyl)cyclopropane-1-sulfonamide

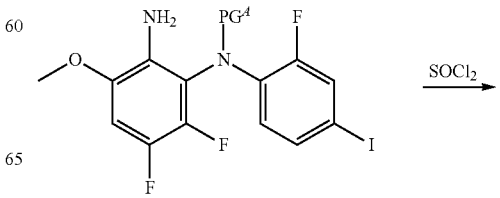

-continued

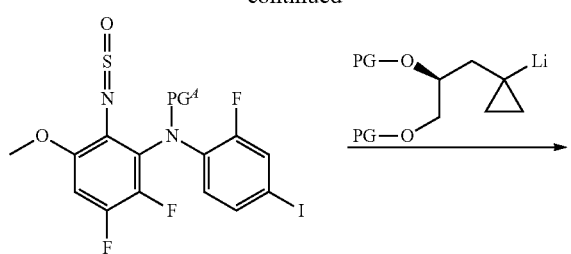

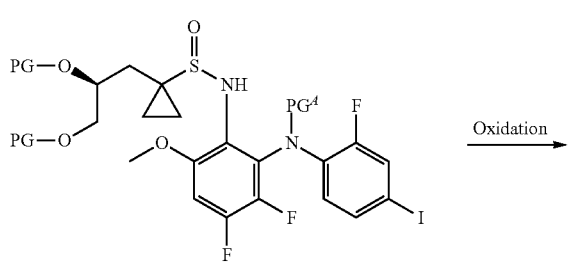

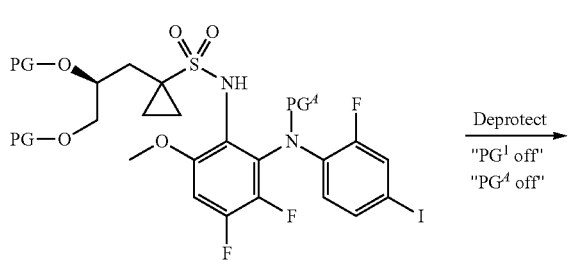

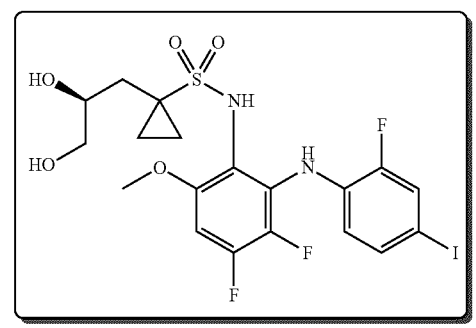

5,6-Difluoro-N¹-(2-fluoro-4-iodophenyl)-3-methoxy-N¹-protected benzene-1,2-diamine is treated with thionyl chloride, converting the primary amine to the thiazate. Coupling with diol protected (1-(2,3-dihydroxypropyl)cyclopropyl) lithium yields the sulfinamide derivative which is oxidized to the sulfonamide. Final removal of protecting groups, as required, yields (R)—N-(3,4-difluoro-2-(2-fluoro-4-iodophenylamino)-6-methoxyphenyl)-1-(2,3-dihydroxypropyl)cyclopropane-1-sulfonamide, (S)—N-(3,4-difluoro-2-(2-fluoro-4-iodophenylamino)-6-methoxyphenyl)-1-(2,3-dihydroxypropyl)cyclopropane-1-sulfonamide or the racemic mixture, depending on the starting material employed.

Method C1:
Synthesis Utilizing Chiral Reagents—(i) Chiral Epoxidation

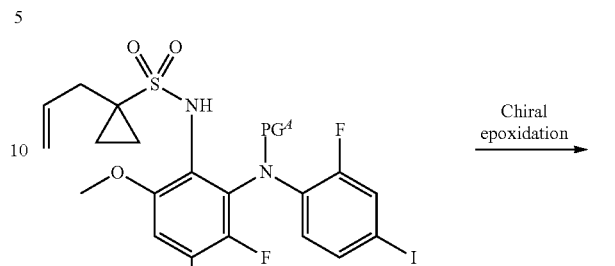

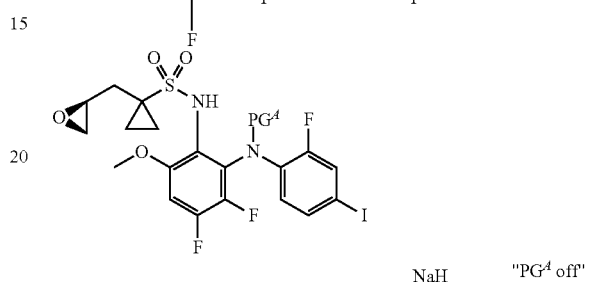

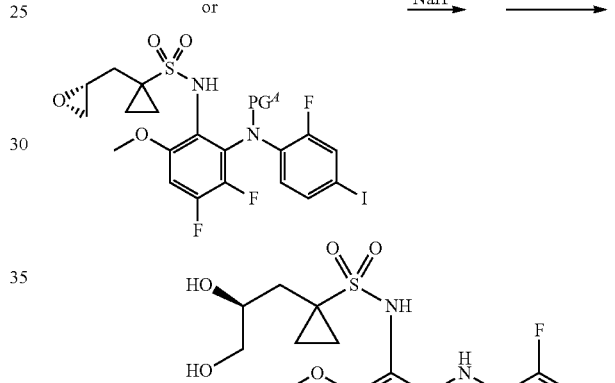

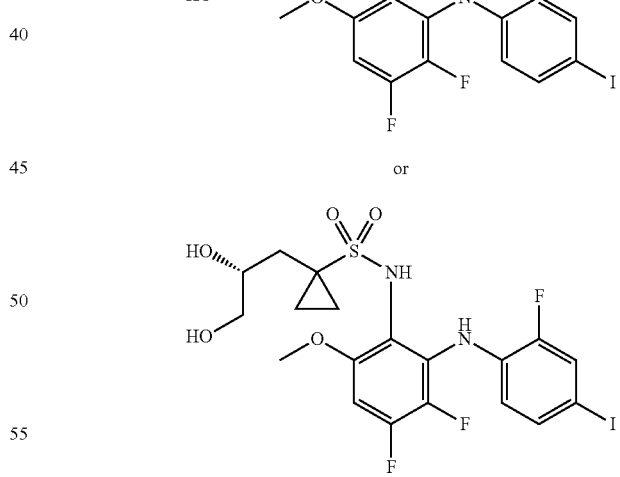

Chiral epoxidation (eg Jacobsen epoxidation (*J. Am. Chem. Soc.*, 1991, 113, 7063-7064 or *J. Am. Chem. Soc.*, 2003, 125, 5250-5251) using sodium hypochlorite/Mn-salen catalyst; or Shi epoxidation (*J. Org. Chem.*, 2007, 72, 4093-4097) using glucose-derived ketones and Oxone) of amine protected 1-allyl-N-(3,4-difluoro-2-(2-fluoro-4-iodophenylamino)-6-methoxyphenyl)cyclopropane-1-sulfonamide, followed by epoxide opening and removal of protecting groups, as required yields the desired chiral products.

Method C2:
Synthesis Utilizing Chiral Reagents—(ii) Chiral Ketone Oxidation

Method C3:
Synthesis Utilizing Chiral Reagents—(iii) Chiral Alkene Oxidation

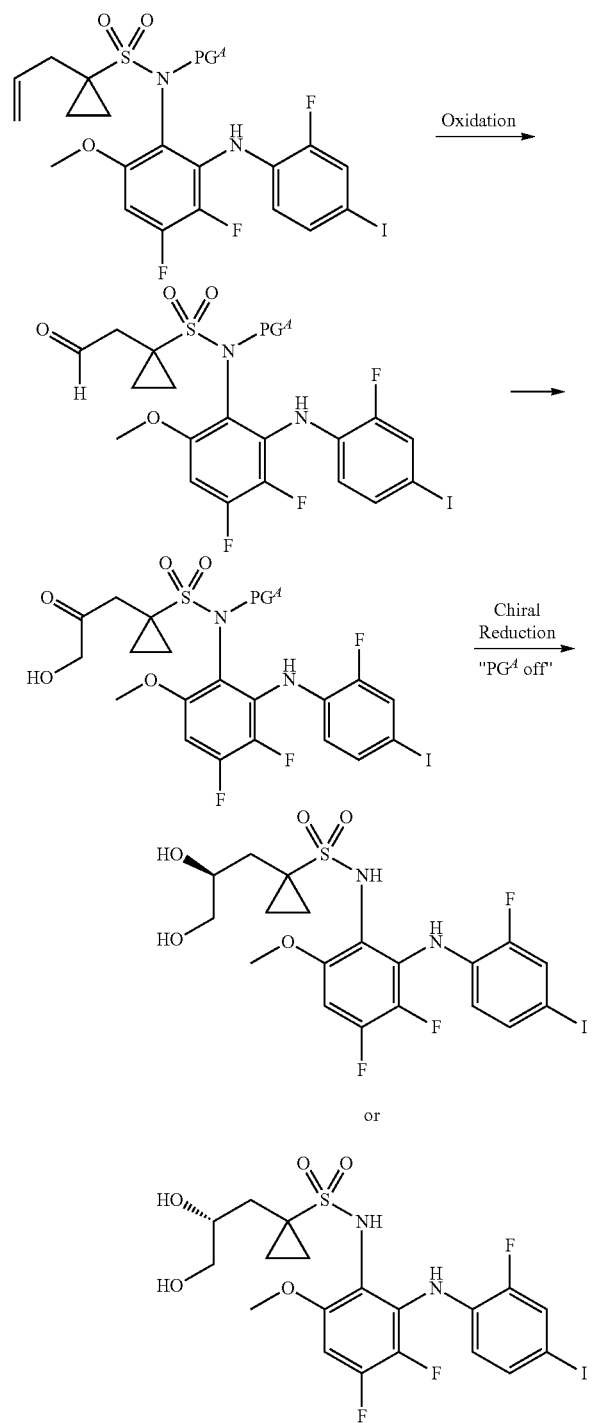

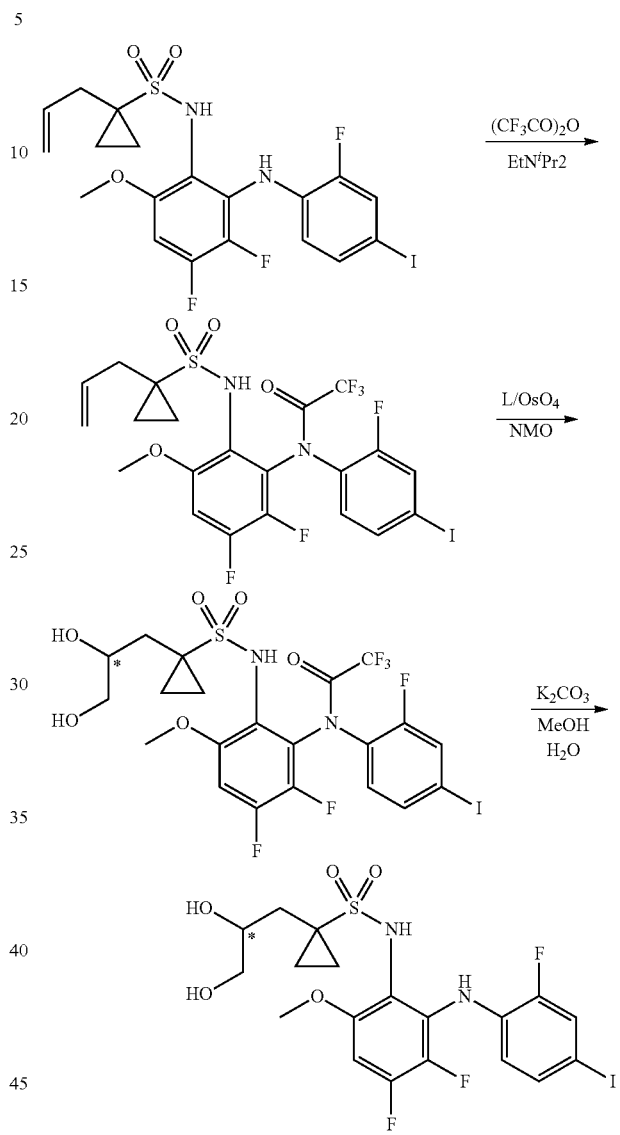

Oxidative cleavage (eg Ozonolysis or Lemieux-Johnson oxidation) of amine protected 1-allyl-N-(3,4-difluoro-2-(2-fluoro-4-iodophenylamino)-6-methoxyphenyl)cyclopropane-1-sulfonamide, followed by conversion to the α-hydroxyketone, chiral reduction of the ketone (eg Corey CBS reduction) and removal of protecting groups, as required yields the desired chiral products.

where L is a chiral auxiliary

Protection of 1-allyl-N-(3,4-difluoro-2-(2-fluoro-4-iodophenylamino)-6-methoxyphenyl)cyclopropane-1-sulfonamide as the trifluoroacetamide, followed by asymmetric dihydroxylation (eg Sharpless asymmetric dihydroylation), and removal of protecting groups, as required yields the desired chiral products.

Method C4:
Synthesis from Chiral Starting Materials

Scheme 7a below shows a synthetic route for the preparation (R)—N-(3,4-difluoro-2-(2-fluoro-4-iodophenylamino)-6-methoxyphenyl)-1-(2,3-dihydroxypropyl)cyclopropane-1-sulfonamide.

Scheme 7b below shows a synthetic route for the preparation (S)—N-(3,4-difluoro-2-(2-fluoro-4-iodophenylamino)-6-methoxyphenyl)-1-(2,3-dihydroxypropyl)cyclopropane-1-sulfonamide.

Scheme 7a: (R)-N-(3,4-difluoro-2-(2-fluoro-4-iodophenylamino)-6-methoxyphenyl)-1-(2,3-dihydroxypropyl)cyclopropane-1-sulfonamide

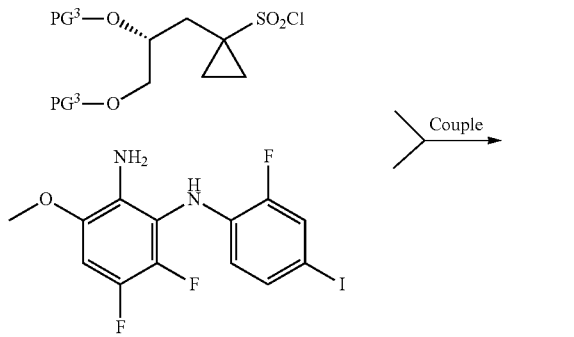

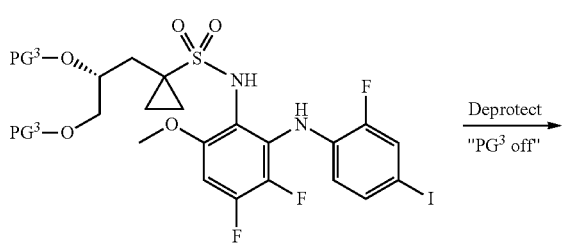

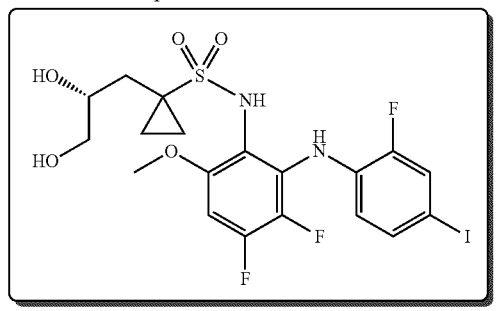

Scheme 7b: (S)-N-(3,4-difluoro-2-(2-fluoro-4-iodophenylamino)-6-methoxyphenyl)-1-(2,3-dihydroxypropyl)cyclopropane-1-sulfonamide

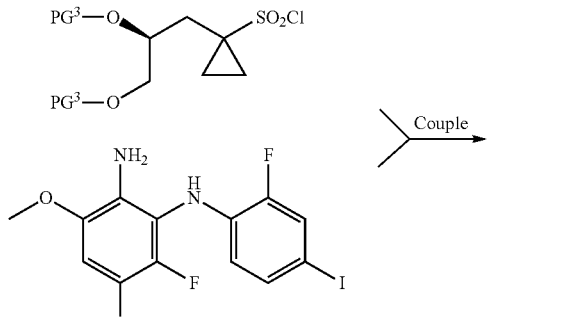

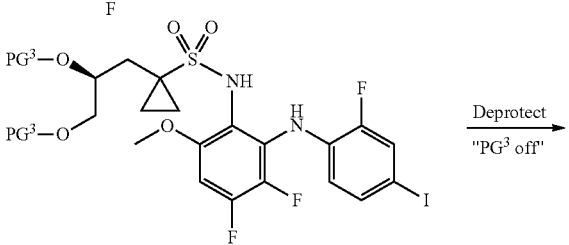

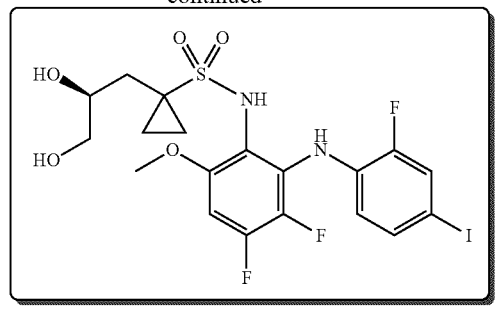

Coupling diol-protected 1-(2,3-dihydroxypropyl)cyclopropane-1-sulfonyl chloride with 5,6-difluoro-$N^1$-(2-fluoro-4-iodophenyl)-3-methoxybenzene-1,2-diamine provides the diol protected product. In some instances the coupling may be performed at elevated temperatures. Final deprotection yields (R)—N-(3,4-difluoro-2-(2-fluoro-4-iodophenylamino)-6-methoxyphenyl)-1-(2,3-dihydroxypropyl)cyclopropane-1-sulfonamide, (S)—N-(3,4-difluoro-2-(2-fluoro-4-iodophenylamino)-6-methoxyphenyl)-1-(2,3-dihydroxypropyl)cyclopropane-1-sulfonamide or the racemic mixture, depending on the starting material employed. Conditions for deprotection will depend on the protecting group(s) used and will be known to one of skill in the art of organic chemistry.

Methods for the preparation of the diol-protected 1-(2,3-dihydroxypropyl)cyclopropane-1-sulfonyl chloride include:

Route i

Via Glycidol-Acetylene Coupling/Halogenation/Cyclopropanation/Sulfonylation:

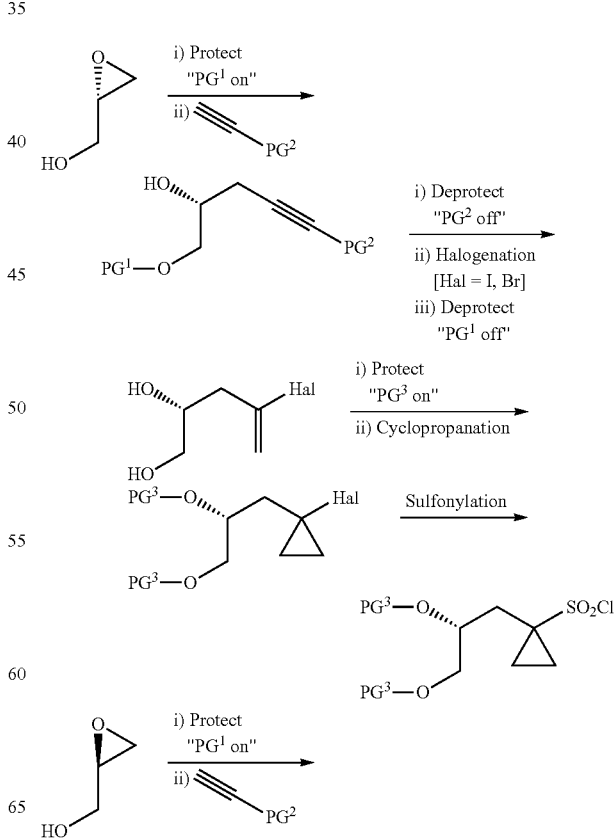

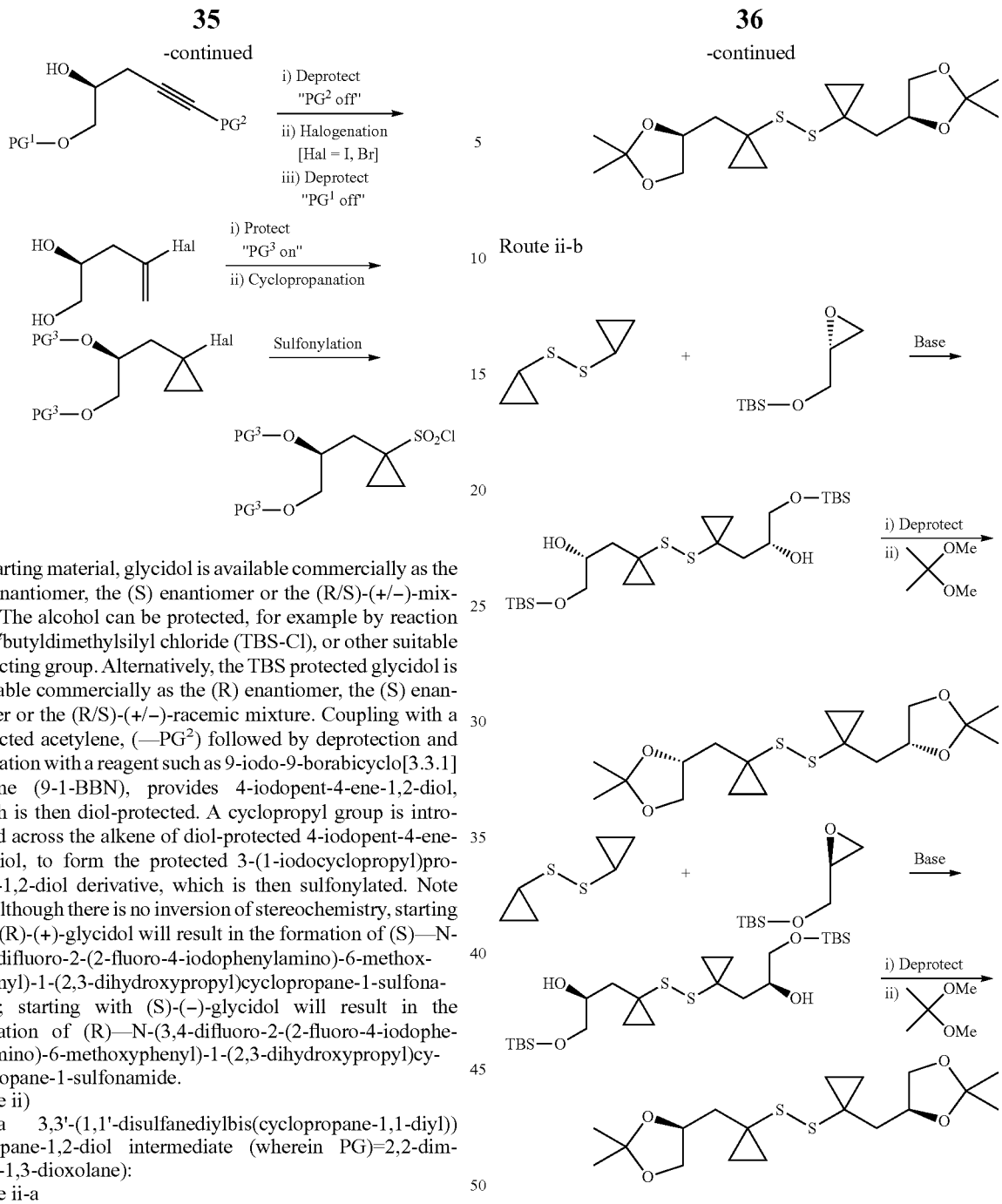

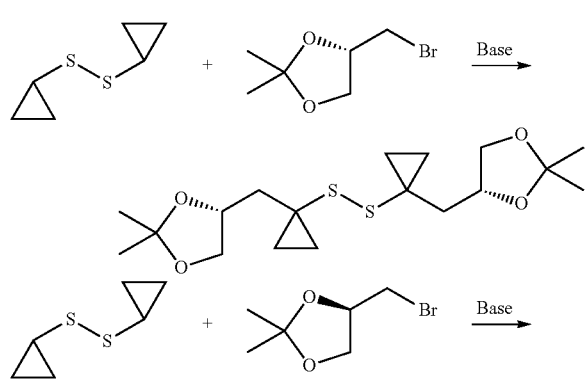

Starting material, glycidol is available commercially as the (R) enantiomer, the (S) enantiomer or the (R/S)-(+/−)-mixture. The alcohol can be protected, for example by reaction with ′butyldimethylsilyl chloride (TBS-Cl), or other suitable protecting group. Alternatively, the TBS protected glycidol is available commercially as the (R) enantiomer, the (S) enantiomer or the (R/S)-(+/−)-racemic mixture. Coupling with a protected acetylene, (—PG$^2$) followed by deprotection and iodination with a reagent such as 9-iodo-9-borabicyclo[3.3.1]nonane (9-1-BBN), provides 4-iodopent-4-ene-1,2-diol, which is then diol-protected. A cyclopropyl group is introduced across the alkene of diol-protected 4-iodopent-4-ene-1,2-diol, to form the protected 3-(1-iodocyclopropyl)propane-1,2-diol derivative, which is then sulfonylated. Note that although there is no inversion of stereochemistry, starting with (R)-(+)-glycidol will result in the formation of (S)—N-(3,4-difluoro-2-(2-fluoro-4-iodophenylamino)-6-methoxyphenyl)-1-(2,3-dihydroxypropyl)cyclopropane-1-sulfonamide; starting with (S)-(−)-glycidol will result in the formation of (R)—N-(3,4-difluoro-2-(2-fluoro-4-iodophenylamino)-6-methoxyphenyl)-1-(2,3-dihydroxypropyl)cyclopropane-1-sulfonamide.

Route ii)

Via 3,3'-(1,1'-disulfanediylbis(cyclopropane-1,1-diyl))dipropane-1,2-diol intermediate (wherein PG)=2,2-dimethyl-1,3-dioxolane):

Route ii-a

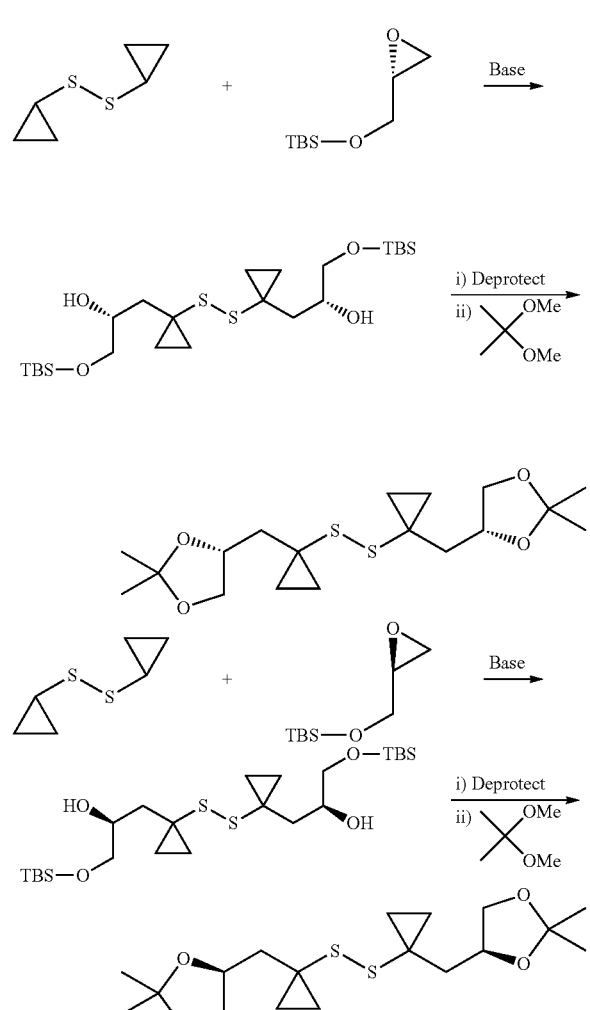

Route ii-b

The 1,2-bis(1-((2,2-dimethyl-1,3-dioxolan-4-yl)methyl)cyclopropyl)disulfane intermediate can be prepared either directly by reacting 1,2-dicyclopropyldisulfane with 4-(bromomethyl)-2,2-dimethyl-1,3-dioxolane (route ii-a), or by coupling 1,2-dicyclopropyldisulfane with tert-butyldimethyl(oxiran-2-ylmethoxy)silane, followed by removal of the TBS protecting group and protection of the resulting diol (route ii-b).

The 1,2-bis(1-((2,2-dimethyl-1,3-dioxolan-4-yl)methyl)cyclopropyl)disulfane can be directly converted to the sulfonyl chloride (route ii-c), or via the sulfonate salt, which is then converted to the chloride (route ii-d). Alternatively, the disulfane can be reduced to the sulfide, which is then oxidized to the sulfonate and converted to the sulfonyl chloride (route ii-e):

Route ii-c

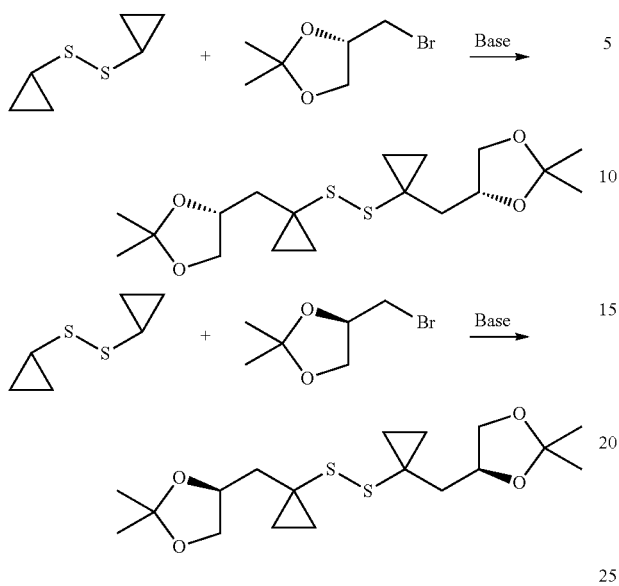

Route ii-d

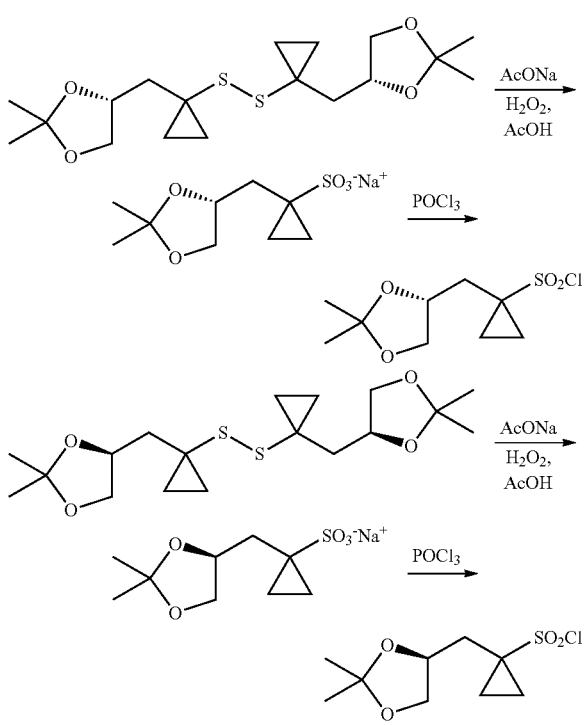

Route ii-e

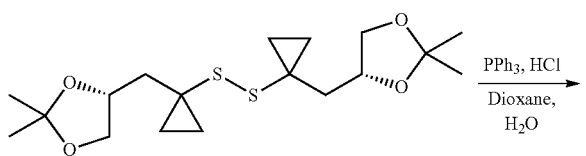

-continued

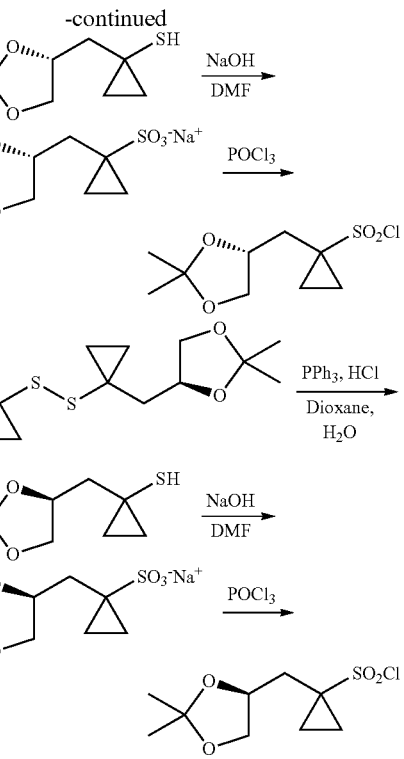

II. Protecting Groups

In the reactions described, it may be necessary to protect reactive alcohol and/or amine functional groups. Protecting groups are used to block some or all alcohol and/or amine functional groups to prevent them from participating in chemical reactions until the protective group is removed. In some embodiments, wherein more than one protective group is required, each protective group is removable by a different means. In other embodiments, wherein more than one protective group is required, multiple protective groups are removable by the same means. In some embodiments, wherein more than one protective group is required, a single protecting group maybe used to protect multiple functionalities (eg a cyclic group). Protective groups can be removed by treatment with acid, base, a nucleophile, hydrogenolysis or by exposure to UV light or a combination thereof. For example, groups such as trityl, dimethoxytrityl, acetal and t-butyldimethylsilyl are acid labile; groups such as methyl, ethyl and acetyl are base labile and groups such as t-butyl carbamate and benzyl are hydrolytically removed. Another form of protecting group is a resin to which a compound or intermediate may be attached. As long as the residue is attached to the resin, that functional group is blocked and cannot react. Once released from the resin, the functional group is available to react. Other protecting groups, plus descriptions of techniques applicable for adding and removing protecting groups are described in "Protecting Groups in Organic Synthesis" by Greene & Wuts, 3$^{rd}$ edition, 1999, John Wiley and Sons, Inc., New York, N.Y., incorporated herein by reference.

In some embodiments, intermediates comprising a protected alcohol are required. Alcohol protecting groups are well known to those of skill in the art of organic chemistry, and are well described in the literature (see for example "Protecting Groups in Organic Synthesis" by Greene & Wuts, 3$^{rd}$ edition, 1999, John Wiley and Sons, Inc., New York, N.Y.; Chapter 2—"Protection for the Hydroxyl Group, Including 1,2- and 1,3-Diols"). Examples of alcohol protecting groups include, but are not limited to substituted methyl ethers, such as methoxymethyl, benzyloxymethyl, p-methoxybenzyloxymethyl, t-butoxymethyl, tetrahydropyranyl, methoxycyclohexyl, methoxytetrahydropyranyl, tetrahydrofuranyl; substituted ethyl ethers, such as ethoxyethyl, t-butyl, allyl, propargyl; substituted benzyl ethers such as p-methoxybenzyl, picolyl, diphenylmethyl, triphenylmethyl; silylethers, such as trimethylsilyl, triisopropylsilyl, t-butyldimethylsilyl, tribenzylsilyl, triphenylsilyl; esters, carbonates, sulfonates and the like.

In some embodiments, intermediates comprising protected 1,2-diols are required. 1,2-Diol protecting groups are well known to those of skill in the art of organic chemistry. Examples of 1,2-diol protecting groups include, but are not limited to 1,3-dioxolane, 2-methyl-1,3-dioxolane, 2,2-dimethyl-1,3-dioxolane, 2-$^t$butyl-1,3-dioxolane, 2-phenyl-1,3-dioxolane, 1,4-dioxaspiro[4.5]decane, di-para-methoxybenzyloxymethyl ether, di-$^t$butyldimethylsilyl ether, and the like:

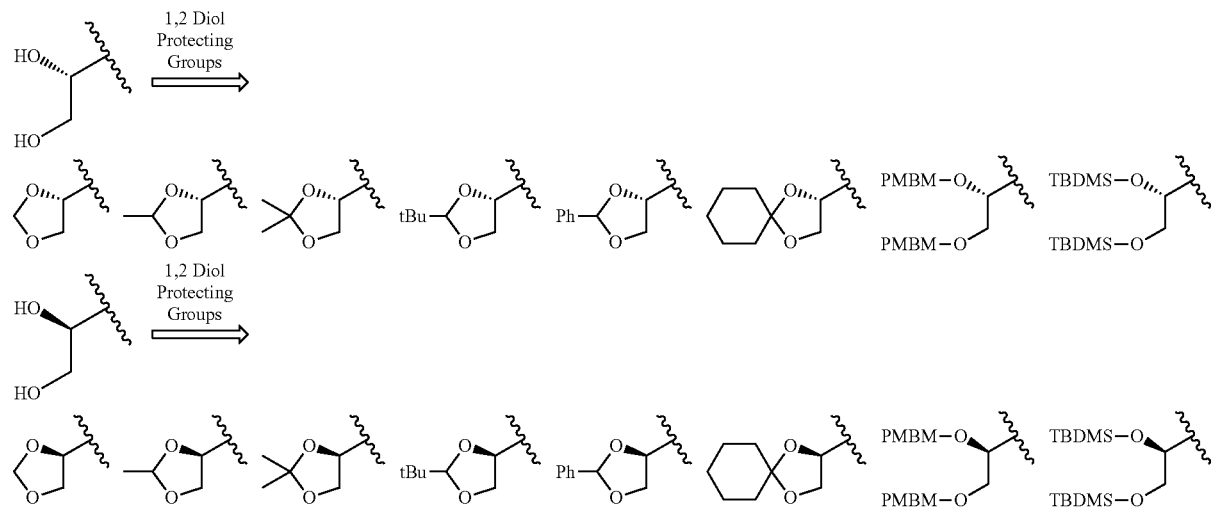

EXAMPLES

The examples and preparations provided below further illustrate and exemplify the compounds of the present invention and methods of preparing such compounds. It is to be understood that the scope of the present invention is not limited in any way by the scope of the following examples and preparations.

Example 1

(R)—N-(3,4-difluoro-2-(2-fluoro-4-iodophenylamino)-6-methoxyphenyl)-1-(2,3-dihydroxypropyl)cyclopropane-1-sulfonamide

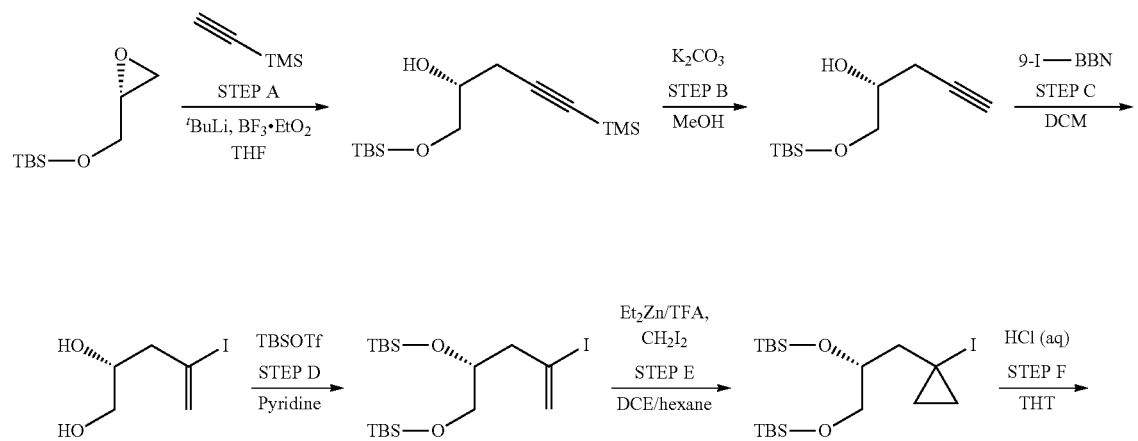

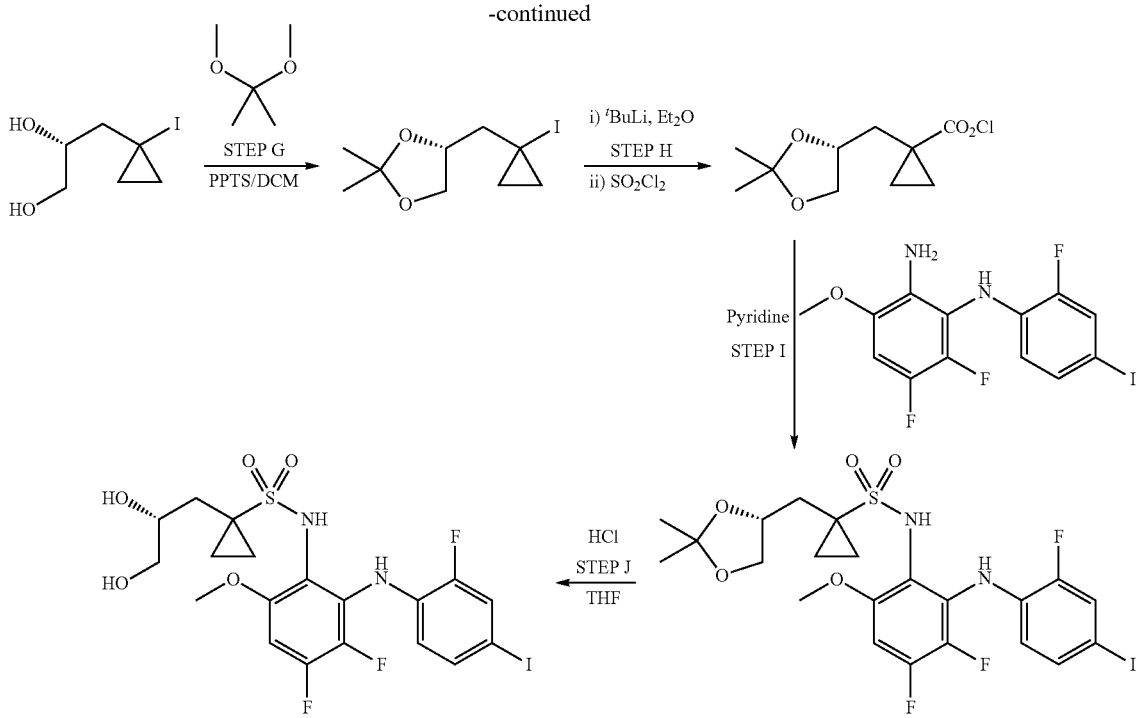

Step A: (R)-1-(tert-butyldimethylsilyloxy)-5-(trimethylsilyl)pent-4-yn-2-ol

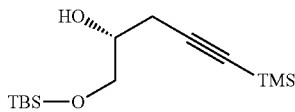

tert-BuLi (12.4 ml, 1.7M, 21.1 mmol) was added to a solution of TMS-acetylene (2.12 g, 21.7 mmol) in THF (40 ml) at −78° C. and the reaction mixture was stirred for an additional 30 min. (R)-tert-butyldimethyl(oxiran-2-ylmethoxy)silane (2 g, 10.6 mmol) and BF$_3$.EtO$_2$ (3 g, 21.1 mmol) were added and stirred at −78° C. for 4.5 hours. The reaction was then quenched by addition of aqueous ammonium chloride solution and the mixture was extracted with ethyl acetate (3×50 mL). The combined organic layers were washed with brine, dried (MgSO$_4$) and concentrated under reduced pressure to afford the desired material in a quantitative yield. The material was used in the next step with no further purification.

Step B: (R)-1-(tert-butyldimethylsilyloxy)pent-4-yn-2-ol

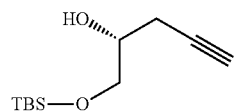

Potassium carbonate (2.14 g, 15.5 mmol) was added to a solution of (R)-1-(tert-butyldimethylsilyloxy)-5-(trimethylsilyl)pent-4-yn-2-ol (3 g, 10.6 mmol) in methanol (100 mL) and the mixture stirred at room temperature for 8 hours. The solvent was removed under reduced pressure and aqueous ammonium chloride solution (100 mL) was added to the resulting oil. The mixture was extracted with ethyl acetate (3×50 mL). The combined organic layers were washed with brine, dried (MgSO4) and concentrated under reduced pressure. The crude material was purified by flash chromatography (biotage) using a gradient of EtOAc in hexane to afford (R)-1-(tert-butyldimethylsilyloxy)pent-4-yn-2-ol (1.81 g, 8.44 mmol, 80%).

$^1$H NMR (CDCl$_3$, 300 MHz): δ 3.78-3.86 (m, 1H), 3.71 (dd, 1H), 3.64 (dd, 1H), 2.52 (d, 1H), 2.36-2.44 (m, 2H), 0.96 (s, 9H), 0.05 (s, 6H).

Step C: (R)-4-Iodopent-4-ene-1,2-diol

9-Iodo-9-borabicyclo[3.3.1]nonane (9-I-BBN) was added dropwise to a solution (R)-1-(tert-butyldimethylsilyloxy)pent-4-yn-2-ol (476 mg, 2.22 mmol) in dichloromethane (2 mL) at 0° C. and the reaction stirred at 0° C. for 4 hours. Glacial acetic acid (0.26 mL) was then added and the mixture was stirred for an additional hour at 0° C. The reaction was quenched by addition of an aqueous mixture of Na$_2$CO$_3$/Na$_2$S$_2$O$_3$ (40 ml, 1:1) and the resulting solution extracted with ethyl acetate (3×30 mL). The combined organic layers were dried (MgSO$_4$) and concentrated under reduced pressure to afford (R)-4-iodopent-4-ene-1,2-diol.

<sup>1</sup>H NMR (CDCl<sub>3</sub>, 300 MHz): δ 6.11 (s, 1H), 5.85 (s, 1H), 3.98-4.07 (m, 1H), 3.74 (dd, 1H), 3.54 (dd, 1H), 2.62 (d, 2H), 2.19 (bs, OH), 1.64 (bs, OH).

Step D: (R)-5-(2-iodoallyl)-2,2,3,3,8,8,9,9-octamethyl-4,7-dioxa-3,8-disiladecane

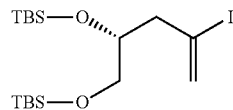

A solution of (R)-4-iodopent-4-ene-1,2-diol (224 mg, 1 mmol) in THF (6 ml) was cooled to 0° C., and pyridine (293 mg, 3.7 mmol) and tert-butyldimethylsilyl trifluoromethanesulfonate (TBSOTf) were added dropwise. The reaction mixture was warmed to room temperature, stirred for an additional 20 mins and the solvents removed under reduced pressure. The crude material was dissolved in chloroform, washed with brine, dried (MgSO<sub>4</sub>) concentrated under reduced pressure, and purified by flash chromatography using a gradient of ethyl acetate in hexane, to afford (R)-5-(2-iodoallyl)-2,2,3,3,8,8,9,9-octamethyl-4,7-dioxa-3,8-disiladecane (254 mg, 56%).

<sup>1</sup>H NMR (CDCl<sub>3</sub>, 500 MHz): δ 6.13 (s, 1H), 5.79 (s, 1H), 3.86-3.95 (m, 1H), 3.64 (dd, J=10, 4 Hz, 1H), 3.49 (dd, J=10, 6 Hz, 1H), 2.52 (d, J=6 Hz, 2H), 2.35 (d, J=4 Hz, OH), 0.89 (s, 18H), 0.04 (s, 12H).

Step E: (R)-5-((1-iodocyclopropyl)methyl)-2,2,3,3,8,8,9,9-octamethyl-4,7-dioxa-3,8-disiladecane

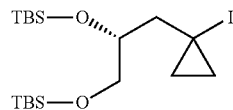

Trifluoroacetic acid (TFA; 281 mg, 2.47 mmol) was added to a solution of diethyl zinc (ZnEt<sub>2</sub>, 2.5 mL, 2.5M in hexane) in DCE (1 mL) at 0° C. and stirred for 35 mins. Diiodomethane (CH<sub>2</sub>I<sub>2</sub>, 66 mg, 2.5 mmol) was then added at 0° C., and the mixture stirred for an additional 20 min. A solution of (R)-5-(2-iodoallyl)-2,2,3,3,8,8,9,9-octamethyl-4,7-dioxa-3,8-disiladecane (step D; 188 mg, 0.41 mmol) in DCE (2 ml) was added and the reaction stirred at room temperature overnight. The reaction was then quenched by addition of a mixture of methanol (5 mL) and brine (0.5 mL). After stirring for an additional hour, the mixture was concentrated under reduced pressure. The crude material was extracted with aq.NH<sub>4</sub>Cl/CHCl<sub>3</sub> and the organic layer washed with brine, dried (MgSO<sub>4</sub>) and concentrated under reduced pressure. The crude material was triturated in hexane and the solution filtered and evaporated to afford (R)-5-((1-iodocyclopropyl)methyl)-2,2,3,3,8,8,9,9-octamethyl-4,7-dioxa-3,8-disiladecane (148 mg, 77%).

<sup>1</sup>H NMR (CDCl<sub>3</sub>, 500 MHz): δ 3.91-3.95 (m, 1H), 3.60 (dd, J=10, 5 Hz, 1H), 3.47 (dd, J=10, 6 Hz, 1H), 1.95 (dd, J=10, 4 Hz, 1H), 1.28 (dd, J=10, 6 Hz, 1H), 0.99-1.07 (m, 2H), 0.75-0.90 (m, 2H), 0.89 (s, 18H), 0.12 (s, 3H), 0.08 (s, 3H), 0.04 (s, 6H).

Step F: (R)-3-(1-iodocyclopropyl)propane-1,2-diol

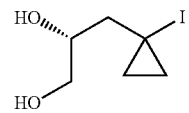

Aqueous HCl solution (0.3 mL, 1N) was added to a solution of (R)-5-(1-iodocyclopropyl)methyl)-2,2,3,3,8,8,9,9-octamethyl-4,7-dioxa-3,8-disiladecane (step E, 281 mg, 0.598 mmol) in THF (2 mL) at 0° C. The mixture was slowly warmed at room temperature and stirred for 24 hours. The reaction was quenched by addition of aqueous NaHCO<sub>3</sub> solution and extracted with ethyl acetate. The combined organic layers were washed with brine, dried (MgSO<sub>4</sub>) and concentrated under reduced pressure to provide (R)-3-(1-iodocyclopropyl)propane-1,2-diol (0.598 mmol), which was used in the next step with no further purification.

Step G: (R)-4-((1-iodocyclopropyl)methyl)-2,2-dimethyl-1,3-dioxolane

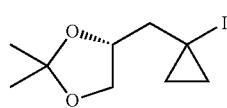

2,2-Dimethoxypropane (140 mg, 1.337 mmol) and pyridinium p-toluenesulfonate (PPTS, 6 mg) were added to a solution of crude (R)-3-(1-iodocyclopropyl)propane-1,2-diol (step F, 0.598 mmol) dissolved in dichloromethane (3 mL) and the mixture stirred at room temperature for 2 hours. Solvents were removed under reduced pressure and the crude product purified by flash chromatography using ethyl acetate/hexane (1:10) eluant to afford (R)-4-((1-iodocyclopropyl)methyl)-2,2-dimethyl-1,3-dioxolane (84 mg, 50%).

<sup>1</sup>H NMR (CDCl<sub>3</sub>, 500 MHz): δ 4.31-4.37 (m, 1H), 4.16 (dd, T=10, 5 Hz, 1H), 3.56 (dd, T=10, 8 Hz, 1H), 1.72-1.80 (m, 2H), 1.35 (s, 6H), 1.04-1.11 (m, 2H), 0.90-0.94 (m, 1H), 0.73-0.77 (m, 1H).

Step H: (R)-1-((2,2-dimethyl-1,3-dioxolan-4-yl)methyl)cyclopropane-1-sulfonyl chloride

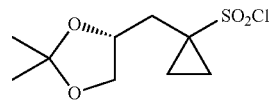

tert-Butyl lithium (0.2 mL, 0.34 mmol, 1.7M) was added to a solution of (R)-4-(1-iodocyclopropyl)methyl)-2,2-dimethyl-1,3-dioxolane (step G, 45 mg, 0.16 mmol) in ether (1 mL) at −78° C. and the mixture stirred at −78° C. for 30 mins. A solution of thionyl chloride (26 μL) in ether (0.5 mL) was then added. The resulting orange solution was warmed to room temperature and concentrated under reduced pressure.

The residue was dissolved in chloroform, filtered and dried under reduced pressure to afford (R)-1-((2,2-dimethyl-1,3-dioxolan-4-yl)methyl)cyclopropane-1-sulfonyl chloride (23.7 mg, 57%).

m/z=255 [M+1]⁻.

Step I: (R)—N-(3,4-difluoro-2-(2-fluoro-4-iodophenylamino)-6-methoxyphenyl)-1-((2,2-dimethyl-1,3-dioxolan-4-yl)methyl)cyclopropane-1-sulfonamide

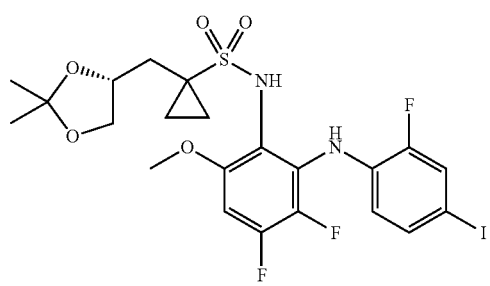 [SMILES: COc1cc(F)c(F)c(Nc2ccc(I)cc2F)c1NS(=O)(=O)C1(C[C@@H]2COC(C)(C)O2)CC1]

A solution of 5,6-difluoro-N¹-(2-fluoro-4-iodophenyl)-3-methoxybenzene-1,2-diamine (22 mg, 0.065 mmol) in dry pyridine (0.8 mL) was added to (R)—N-(3,4-difluoro-2-(2-fluoro-4-iodophenylamino)-6-methoxyphenyl)-1-((2,2-dimethyl-1,3-dioxolan-4-yl)methyl)cyclopropane-1-sulfonamide (step h) and the mixture stirred at room temperature overnight. The solvent was then removed under reduced pressure and the residue dissolved in ethyl acetate, washed with brine, dried (MgSO₄) and concentrated to afford crude (R)—N-(3,4-difluoro-2-(2-fluoro-4-iodophenylamino)-6-methoxyphenyl)-1-((2,2-dimethyl-1,3-dioxolan-4-yl)methyl)cyclopropane-1-sulfonamide, used without further purification in the next step.

m/z=611 [M-1]⁻

Step J: (R)—N-(3,4-difluoro-2-(2-fluoro-4-iodophenylamino)-6-methoxyphenyl)-1-(2,3-dihydroxypropyl)cyclopropane-1-sulfonamide

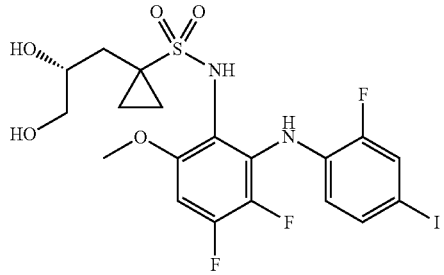 [SMILES: COc1cc(F)c(F)c(Nc2ccc(I)cc2F)c1NS(=O)(=O)C1(C[C@@H](O)CO)CC1]

Crude (R)—N-(3,4-difluoro-2-(2-fluoro-4-iodophenylamino)-6-methoxyphenyl)-1-((2,2-dimethyl-1,3-dioxolan-4-yl)methyl)cyclopropane-1-sulfonamide was dissolve in a mixture of THF (1 mL) and HCl (1.2N, 0.15 ml) and stirred overnight at room temperature. The solvents were removed under reduced pressure and the residue dissolved in ethyl acetate. The organic phase was washed with aqueous NaHCO₃, dried (Na₂SO₄), and concentrated to afford (R)—N-(3,4-difluoro-2-(2-fluoro-4-iodophenylamino)-6-methoxyphenyl)-1-(2,3-dihydroxypropyl)cyclopropane-1-sulfonamide (1.4 mg, crude).

The compound was analyzed by normal-phase HPLC using a CHIRALPAK AD-H column (20×250 mm) at room temperature, using a mobile phase consisting hexane and 2-propanol (80:20) at 12 mL/min. The detection was carried out at 254 nm. The retention time was determined to be 22 min corresponding to the retention time of (+)N-(3,4-difluoro-2-(2-fluoro-4-iodophenylamino)phenyl)-1-(2,3-dihydroxypropyl)cyclopropane-1-sulfonamide.

FIG. 1(a) is the HPLC trace of the crude material, co-injected with an authentic sample of the (−) enantiomer (obtained via chiral separation of the racemic mixture of both isomers).

FIG. 1(b) is the HPLC trace of the crude material

FIG. 1(c) is the HPLC trace of the crude material, co-injected with an authentic sample of the (+) enantiomer (obtained via chiral separation of the racemic mixture of both isomers).

Example 2

(S)—N-(3,4-difluoro-2-(2-fluoro-4-iodophenylamino)-6-methoxyphenyl)-1-(2,3-dihydroxypropyl)cyclopropane-1-sulfonamide

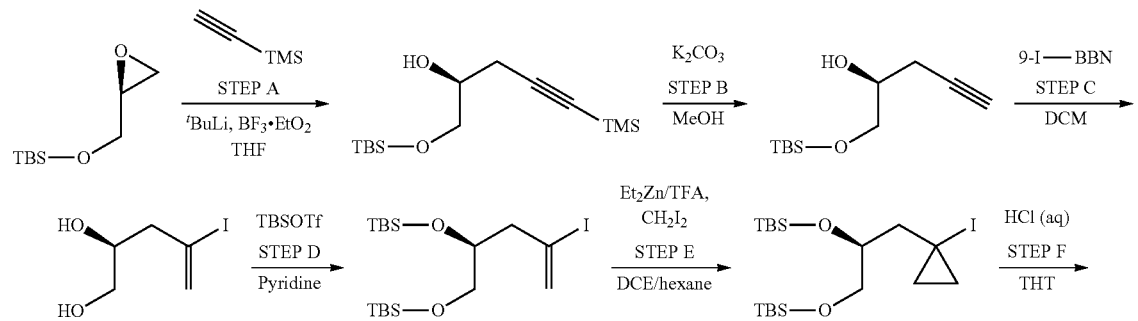

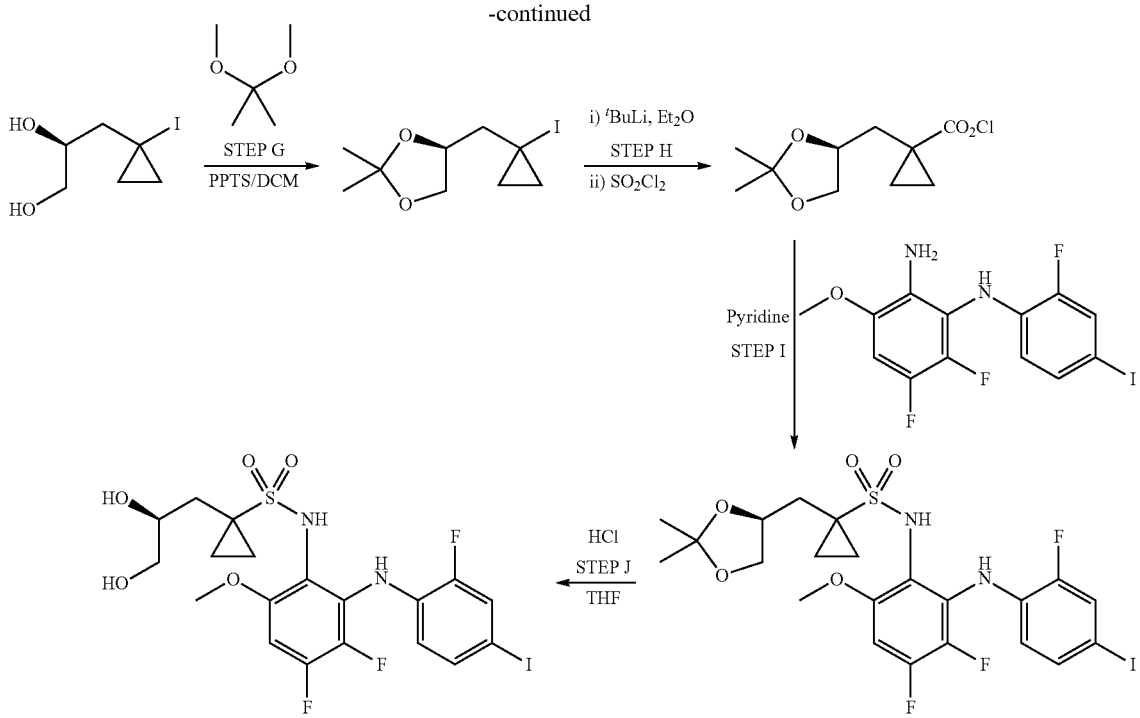

Step A: (S)-1-(tert-butyldimethylsilyloxy)-5-(trimethylsilyl)pent-4-yn-2-ol

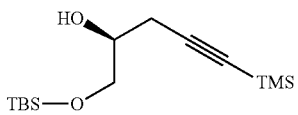

tert-Butyl lithium (2 eq) is added to a solution of TMS-acetylene (2 eq) in THF at −78° C. and the reaction mixture stirred for an additional 30 min. (S)-tert-butyldimethyl(oxiran-2-ylmethoxy)silane (1 eq) and $BF_3.EtO_2$ (2 eq) are added and stirred at −78° C. for 4.5 hours. The reaction is quenched by addition of aqueous ammonium chloride solution and extracted with ethyl acetate (3×). The combined organic layers are washed with brine, dried ($MgSO_4$) and concentrated under reduced pressure to afford (S)-1-(tert-butyldimethylsilyloxy)-5-(trimethylsilyl)pent-4-yn-2-ol.

Step B: (S)-1-(tert-butyldimethylsilyloxy)pent-4-yn-2-ol

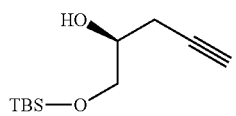

Potassium carbonate (1.5 eq) is added to a solution of (R)-1-(tert-butyldimethylsilyloxy)-5-(trimethylsilyl)pent-4-yn-2-ol (1 eq) in methanol and the mixture stirred at room temperature for 8 hours. The solvent is removed under reduced pressure and aqueous ammonium chloride solution added. The mixture is extracted with ethyl acetate (3×) and the combined organic layers washed with brine, dried (MgSO4), concentrated under reduced pressure and purified by flash chromatography (biotage) using a gradient of EtOAc in hexane.

Step C: (S)-4-Iodopent-4-ene-1,2-diol

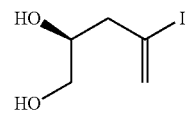

9-Iodo-9-borabicyclo[3.3.1]nonane (9-I-BBN) is added dropwise to a solution (S)-1-(tert-butyldimethylsilyloxy)pent-4-yn-2-ol in dichloromethane at 0° C. and the reaction stirred at 0° C. for 4 hours. Glacial acetic acid is added and the mixture was stirred for an additional hour at 0° C. The reaction is quenched by addition of an aqueous mixture of $Na_2CO_3/Na_2S_2O_3$ (40 ml, 1:1), extracted with ethyl acetate (3×) and the combined organic layers dried ($MgSO_4$) and concentrated under reduced pressure to afford (S)-4-iodo-pent-4-ene-1,2-diol.

Step D: (S)-5-(2-iodoallyl)-2,2,3,3,8,8,9,9-octamethyl-4,7-dioxa-3,8-disiladecane

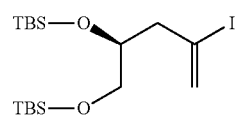

A solution of (S)-4-iodopent-4-ene-1,2-diol (1 eq) in THF is cooled to 0° C., and pyridine (3.7 eq) and tert-butyldimethylsilyl trifluoromethanesulfonate (TBSOTf) added dropwise. The reaction mixture is warmed to room temperature, stirred for an additional 20 mins and the solvents removed under reduced pressure. The crude material is dissolved in chloroform, washed with brine, dried (MgSO$_4$) concentrated under reduced pressure, and purified by flash chromatography using a gradient of ethyl acetate in hexane, to afford (S)-5-(2-iodoallyl)-2,2,3,3,8,8,9,9-octamethyl-4,7-dioxa-3,8-disiladecane.

Step E: (S)-5-((1-iodocyclopropyl)methyl)-2,2,3,3,8,8,9,9-octamethyl-4,7-dioxa-3,8-disiladecane

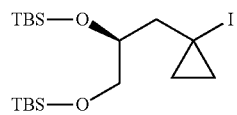

Trifluoroacetic acid (8 eq) is added to a solution of diethyl zinc (16 eq) in DCE at 0° C. and stirred for 35 mins. Diiodomethane (8 eq) is added at 0° C., and the mixture stirred for an additional 20 min. A solution of (S)-5-(2-iodoallyl)-2,2,3,3,8,8,9,9-octamethyl-4,7-dioxa-3,8-disiladecane (1 eq) in DCE is added and the reaction stirred at room temperature overnight. The reaction is quenched by addition of a mixture of methanol and brine. After stirring for an additional hour, the mixture is concentrated under reduced pressure. The crude material is extracted with aqueous NH$_4$Cl/CHCl$_3$ and the organic layer washed with brine, dried (MgSO$_4$) and concentrated under reduced pressure. The crude material is triturated in hexane and the solution filtered and evaporated to afford (S)-5-((1-iodocyclopropyl)methyl)-2,2,3,3,8,8,9,9-octamethyl-4,7-dioxa-3,8-disiladecane.

Step F: (S)-3-(1-iodocyclopropyl)propane-1,2-diol

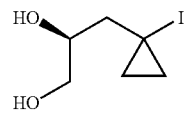

Aqueous HCl solution is added to a solution of (S)-5-((1-iodocyclopropyl)methyl)-2,2,3,3,8,8,9,9-octamethyl-4,7-dioxa-3,8-disiladecane in THF at 0° C. The mixture is slowly warmed to room temperature and stirred for 24 hours. The reaction is quenched by addition of aqueous NaHCO$_3$ solution, extracted with ethyl acetate, and the combined organic layers washed with brine, dried (MgSO$_4$) and concentrated under reduced pressure to provide (S)-3-(1-iodocyclopropyl)propane-1,2-diol (0.598 mmol).

Step G: (S)-4-((1-iodocyclopropyl)methyl)-2,2-dimethyl-1,3-dioxolane

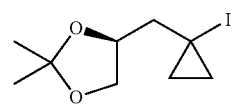

2,2-Dimethoxypropane and pyridinium p-toluenesulfonate are added to a solution of (S)-3-(1-iodocyclopropyl)propane-1,2-diol dissolved in dichloromethane and the mixture stirred at room temperature for 2 hours. Solvents are removed under reduced pressure and the crude product purified by flash chromatography using ethyl acetate/hexane (1:10) eluant.

Step H: (S)-1-((2,2-dimethyl-1,3-dioxolan-4-yl)methyl)cyclopropane-1-sulfonyl chloride

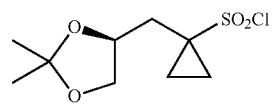

tert-Butyl lithium (2 eq) is added to a solution of (S)-4-(1-iodocyclopropyl)methyl)-2,2-dimethyl-1,3-dioxolane (1 eq) in ether at −78° C. and the mixture stirred at −78° C. for 30 mins. A solution of thionyl chloride in ether is added, the mixture warmed to room temperature and concentrated under reduced pressure. The residue is dissolved in chloroform, filtered and dried under reduced pressure.

Step I: (S)—N-(3,4-difluoro-2-(2-fluoro-4-iodophenylamino)-6-methoxyphenyl)-1-((2,2-dimethyl-1,3-dioxolan-4-yl)methyl)cyclopropane-1-sulfonamide

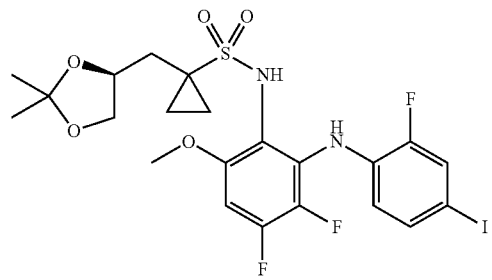 [SMILES: COc1cc(F)c(F)c(Nc2ccc(I)cc2F)c1NS(=O)(=O)C1(C[C@H]2COC(C)(C)O2)CC1]

A solution of 5,6-difluoro-N$^1$-(2-fluoro-4-iodophenyl)-3-methoxybenzene-1,2-diamine in dry pyridine is added to (S)—N-(3,4-difluoro-2-(2-fluoro-4-iodophenylamino)-6-methoxyphenyl)-1-((2,2-dimethyl-1,3-dioxolan-4-yl)methyl)cyclopropane-1-sulfonamide and the mixture stirred at room temperature overnight. The solvent is removed under reduced pressure and the residue dissolved in ethyl acetate, washed with brine, dried (MgSO$_4$) and concentrated.

Step J: (S)—N-(3,4-difluoro-2-(2-fluoro-4-iodophenylamino)-6-methoxyphenyl)-1-(2,3-dihydroxypropyl)cyclopropane-1-sulfonamide

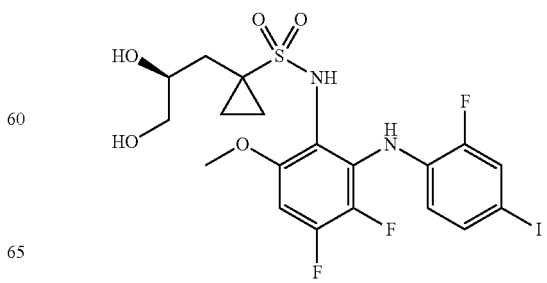

(S)—N-(3,4-difluoro-2-(2-fluoro-4-iodophenylamino)-6-methoxyphenyl)-1-((2,2-dimethyl-1,3-dioxolan-4-yl)methyl)cyclopropane-1-sulfonamide is dissolved in a mixture of THF and HCl and stirred overnight at room temperature. The solvents are removed under reduced pressure and the residue dissolved in ethyl acetate. The organic phase is washed with aqueous NaHCO₃, dried (Na₂SO₄), and concentrated.

Example 3

(R)-3-(2,2-dimethyl-1,3-dioxolan-4-yl)prop-1-ene-2-sulfonyl chloride

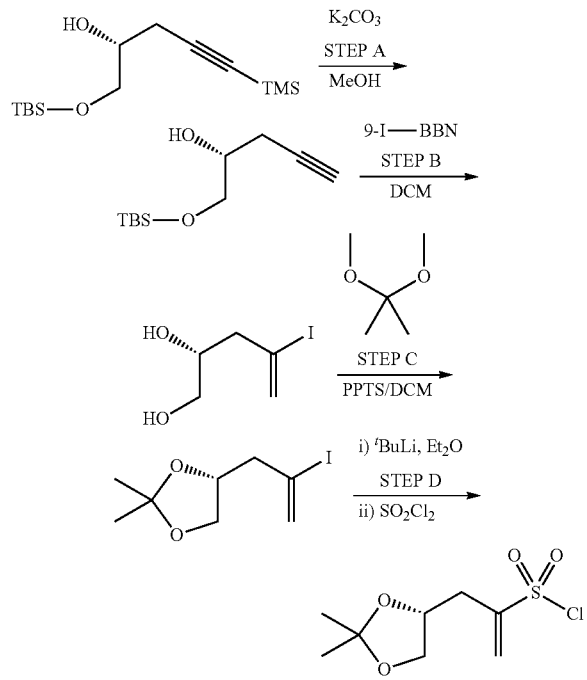

Step A: (R)-1-(tert-butyldimethylsilyloxy)pent-4-yn-2-ol

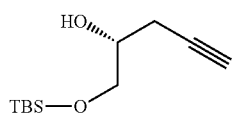

Potassium carbonate (2.14 g, 15.5 mmol) was added to a solution of (R)-1-(tert-butyldimethylsilyloxy)-5-(trimethylsilyl)pent-4-yn-2-ol (3 g, 10.6 mmol) in methanol (100 mL) and the mixture stirred at room temperature for 8 hours. The solvent was removed under reduced pressure and aqueous ammonium chloride solution (100 mL) was added to the resulting oil. The mixture was extracted with ethyl acetate (3×50 mL). The combined organic layers were washed with brine, dried (MgSO4) and concentrated under reduced pressure. The crude material was purified by flash chromatography (biotage) using a gradient of EtOAc in hexane to afford (R)-1-(tert-butyldimethylsilyloxy)pent-4-yn-2-ol (1.81 g, 8.44 mmol, 80%).

¹H NMR (CDCl₃, 300 MHz): δ 3.78-3.86 (m, 1H), 3.71 (dd, 1H), 3.64 (dd, 1H), 2.52 (d, 1H), 2.36-2.44 (m, 2H), 0.96 (s, 9H), 0.05 (s, 6H).

Step B: (R)-4-Iodopent-4-ene-1,2-diol

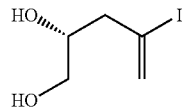

9-Iodo-9-borabicyclo[3.3.1]nonane (9-I-BBN) was added dropwise to a solution (R)-1-(tert-butyldimethylsilyloxy)pent-4-yn-2-ol (476 mg, 2.22 mmol) in dichloromethane (2 mL) at 0° C. and the reaction stirred at 0° C. for 4 hours. Glacial acetic acid (0.26 mL) was then added and the mixture was stirred for an additional hour at 0° C. The reaction was quenched by addition of an aqueous mixture of Na₂CO₃/Na₂S₂O₃ (40 ml, 1:1) and the resulting solution extracted with ethyl acetate (3×30 mL). The combined organic layers were dried (MgSO₄) and concentrated under reduced pressure to afford (R)-4-iodopent-4-ene-1,2-diol.

¹H NMR (CDCl₃, 300 MHz): δ 6.11 (s, 1H), 5.85 (s, 1H), 3.98-4.07 (m, 1H), 3.74 (dd, 1H), 3.54 (dd, 1H), 2.62 (d, 2H), 2.19 (bs, OH), 1.64 (bs, OH).

Step C: (R)-4-(2-iodoallyl)-2,2-dimethyl-1,3-dioxolane

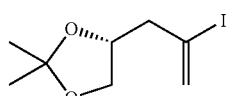

2,2-Dimethoxypropane and pyridinium p-toluenesulfonate (PPTS) are added to a solution of (R)-4-iodopent-4-ene-1,2-diol in dichloromethane and the mixture stirred at room temperature for 2 hours. Solvents are removed under reduced pressure and the crude product purified by flash chromatography using ethyl acetate/hexane (1:10) eluant.

Step D: (R)-3-(2,2-dimethyl-1,3-dioxolan-4-yl)prop-1-ene-2-sulfonyl chloride

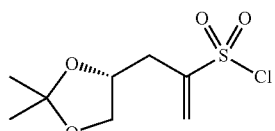

tert-Butyl lithium is added to a solution of (R)-4-(2-iodoallyl)-2,2-dimethyl-1,3-dioxolane in ether at −78° C. and the mixture stirred at −78° C. for 30 mins. A solution of thionyl chloride in ether is then added, the mixture warmed to room temperature and concentrated under reduced pressure. The residue is dissolved in chloroform, filtered and dried under reduced pressure.

Example 4

(S)-3-(2,2-dimethyl-1,3-dioxolan-4-yl)prop-1-ene-2-sulfonyl chloride

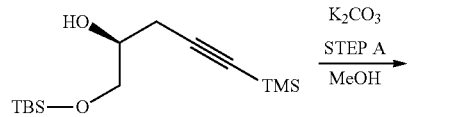

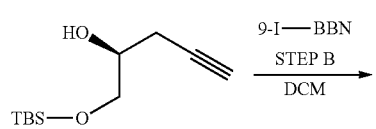

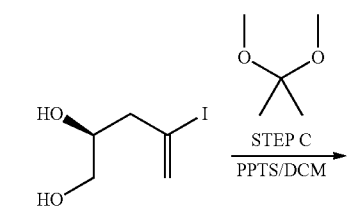

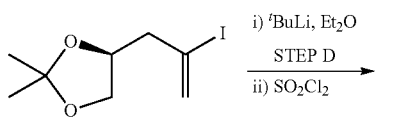

Step A: (S)-1-(tert-butyldimethylsilyloxy)pent-4-yn-2-ol

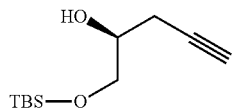

Potassium carbonate is added to a solution of (S)-1-(tert-butyldimethylsilyloxy)-5-(trimethylsilyl)pent-4-yn-2-ol in methanol and the mixture stirred at room temperature for 8 hours. The solvent is removed under reduced pressure, aqueous ammonium chloride solution added, and the mixture extracted with ethyl acetate (3×). The combined organic layers are washed with brine, dried ($MgSO_4$), concentrated under reduced pressure and purified by flash chromatography (biotage; ethyl acetate/hexane gradient).

Step B: (S)-4-Iodopent-4-ene-1,2-diol

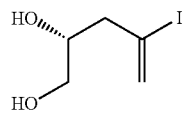

9-Iodo-9-borabicyclo[3.3.1]nonane (9-I-BBN) is added dropwise to a solution (S)-1-(tert-butyldimethylsilyloxy)pent-4-yn-2-ol in dichloromethane at 0° C. and the reaction stirred at 0° C. for 4 hours. Glacial acetic acid is added and the mixture stirred for an additional hour at 0° C. An aqueous mixture of $Na_2CO_3/Na_2S_2O_3$ (1:1) is added and the resulting solution extracted with ethyl acetate (3×). The combined organic layers are dried ($MgSO_4$) and concentrated under reduced pressure.

Step C: (S)-4-(2-iodoallyl)-2,2-dimethyl-1,3-dioxolane

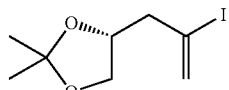

2,2-Dimethoxypropane and pyridinium p-toluenesulfonate (PPTS) are added to a solution of (S)-4-iodopent-4-ene-1,2-diol in dichloromethane and the mixture stirred at room temperature for 2 hours. Solvents are removed under reduced pressure and the crude product purified by flash chromatography using ethyl acetate/hexane (1:10) eluant.

Step D: (S)-3-(2,2-dimethyl-1,3-dioxolan-4-yl)prop-1-ene-2-sulfonyl chloride

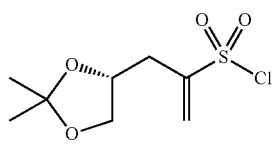

tert-Butyl lithium is added to a solution of (S)-4-(2-iodoallyl)-2,2-dimethyl-1,3-dioxolane in ether at −78° C. and the mixture stirred at −78° C. for 30 mins. A solution of thionyl chloride in ether is then added, the mixture warmed to room temperature and concentrated under reduced pressure. The residue is dissolved in chloroform, filtered and dried under reduced pressure.

Example 5

(R)—N-(3,4-Difluoro-2-(2-fluoro-4-iodophenylamino)-6-methoxyphenyl)-3-(2,2-dimethyl-1,3-dioxolan-4-yl)prop-1-ene-2-sulfonamide

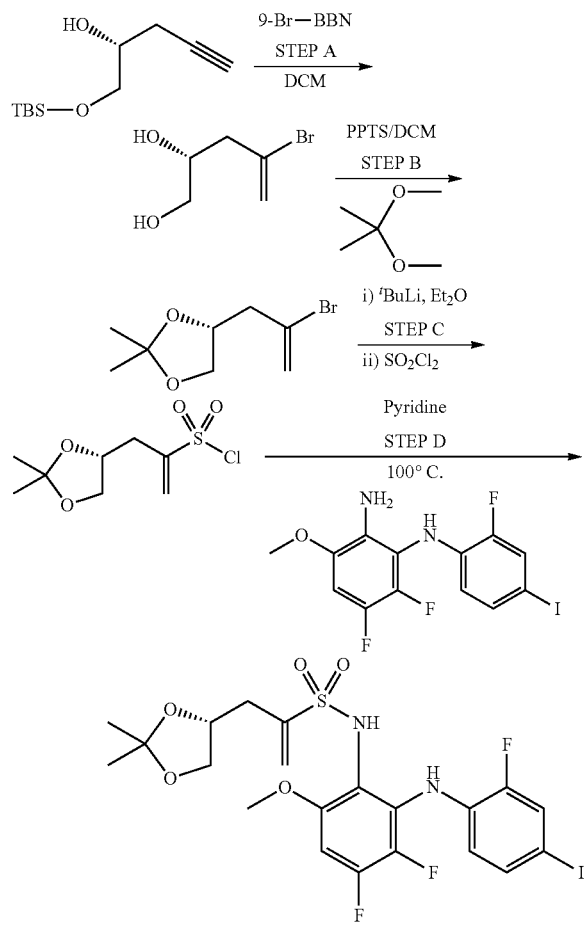

Step A: (R)-4-bromopent-4-ene-1,2-diol

A solution 9-bromo-9-borabicyclo[3.3.1]nonane (9-Br-BBN) in dichloromethane (1M, 10.6 mL) was added dropwise to a solution of (R)-1-(tert-butyldimethylsilyloxy)pent-4-yn-2-ol (755 mg, 3.53 mmol) in dichloromethane (4 mL) at 0° C., and the mixture stirred at 0° C. for 4 hours. Glacial acetic acid (0.65 ml, 11.35 mmol) was added and stirring continued at 0° C. for an additional 1 hour. Ethanolamine (2.5 mL, 41.5 mmol) was added and the mixture allowed to warm to room temperature. The reaction was quenched by addition of an aqueous mixture of $Na_2CO_3/Na_2S_2O_3$ (40 mL, 1:1), extracted with ethyl acetate (3×30 mL), and the combined organic layers dried ($MgSO_4$) and concentrated under reduced pressure to afford (R)-4-bromopent-4-ene-1,2-diol. m/z=182 [M+1]⁻.

Step B: (R)-4-(2-iodoallyl)-2,2-dimethyl-1,3-dioxolane

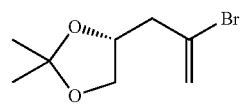

2,2 Dimethoxypropane (993 mg, 9.5 mmol) and pyridinium p-toluenesulfonate (PPTS, 320 mg, 1.27 mmol) were added to a solution of (R)-4-bromopent-4-ene-1,2-diol (1.15 g, 6.36 mmol) in dichloromethane (15 mL) and the mixture stirred at room temperature for 4 hours. Solvents were removed under reduced pressure and the crude product purified by flash chromatography (ethyl acetae:hexane, 1:10 eluant) to afford (R)-4-(2-iodoallyl)-2,2-dimethyl-1,3-dioxolane (1.12 g, 80%).

$^1$H NMR (500 MHz, CHLOROFORM-d) δ ppm 1.34 (s, 3H), 1.39 (s, 3H), 2.52 (dd, J=14.49, 6.05 Hz, 1H), 2.73 (dd, J=14.67, 6.60 Hz, 1H), 3.60 (dd, J=8.16, 6.14 Hz, 1H), 4.06 (dd, J=8.07, 6.05 Hz, 1H), 4.34 (quin, J=6.28 Hz, 1H), 5.78 (d, J=1.10 Hz, 1H), 6.13 (d, J=1.10 Hz, 1H).

Step C: (R)-3-(2,2-dimethyl-1,3-dioxolan-4-yl)prop-1-ene-2-sulfonyl chloride

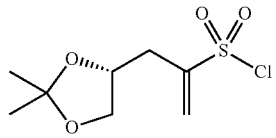

A solution of tert-butyl lithium in hexane (1.7M, 7.65 mL) was added dropwise to a solution of (R)-4-(2-iodoallyl)-2,2-dimethyl-1,3-dioxolane (1.21, 6.5 mmol) in diethyl ether (12 mL) at −78° C., and the reaction stirred at −78° C. for 30 min. Sulfuryl dichloride ($SO_2Cl_2$, 538 µL, 6.5 mmol) was added, the mixture warmed to room temperature and the solvents removed under reduced pressure. The product was used in the next step with no further purification.

Step D: (R)—N-(3,4-difluoro-2-(2-fluoro-4-iodophenylamino)-6-methoxyphenyl)-3-(2,2-dimethyl-1,3-dioxolan-4-yl)prop-1-ene-2-sulfonamide

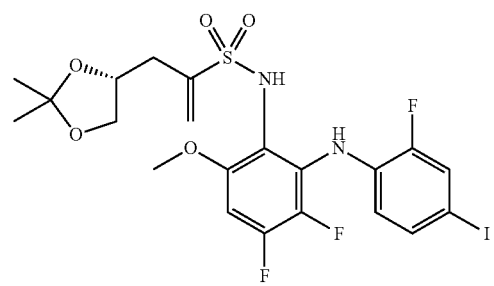 [SMILES: C=C(C[C@@H]1COC(C)(C)O1)S(=O)(=O)Nc1c(OC)cc(F)c(F)c1Nc1ccc(I)cc1F]

(R)-3-(2,2-dimethyl-1,3-dioxolan-4-yl)prop-1-ene-2-sulfonyl chloride from STEP C was dissolved in pyridine (12 mL) and 5,6-difluoro-N[1]-(2-fluoro-4-iodophenyl)-3-methoxybenzene-1,2-diamine (2.56 g, 6.5 mmol) added. The solution was stirred at 100° C. for 2 hours and then partitioned with water and ethyl acetate. The organic layer was washed with brine, dried (MgSO$_4$), concentrated under reduced pressure and purified by flash column chromatography on silica (30% ethyl acetate/hexanes eluant) to afford (R)—N-(3,4-difluoro-2-(2-fluoro-4-iodophenylamino)-6-methoxyphenyl)-3-(2,2-dimethyl-1,3-dioxolan-4-yl)prop-1-ene-2-sulfonamide (651 mg, 17%).

$^1$H NMR (500 MHz, CHLOROFORM-d) δ ppm 1.32 (s, 3H), 1.39 (s, 3H), 2.57-2.64 (m, 1H), 2.64-2.72 (m, 1H), 3.59 (dd, J=8.25, 6.60 Hz, 1H), 3.78 (s, 3H), 4.00-4.13 (m, 1H), 4.27-4.36 (m, 1H), 5.72 (s, 1H), 5.92 (s, 1H), 6.21 (s, 1H), 6.41 (td, J=8.62, 5.14 Hz, 1H), 6.47 (dd, J=11.19, 6.60 Hz, 1H), 7.15 (s, 1H) 7.25 (s, 1H), 7.35 (dd, J=10.45, 1.83 Hz, 1H).

Example 6

(S)—N-(3,4-difluoro-2-(2-fluoro-4-iodophenylamino)-6-methoxyphenyl)-3-(2,2-dimethyl-1,3-dioxolan-4-yl)prop-1-ene-2-sulfonamide

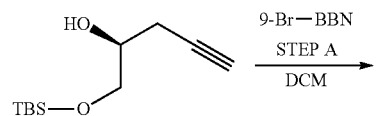

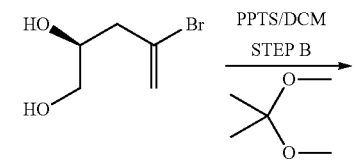

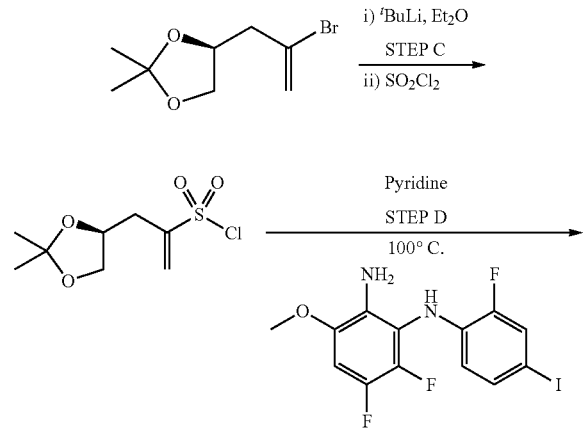

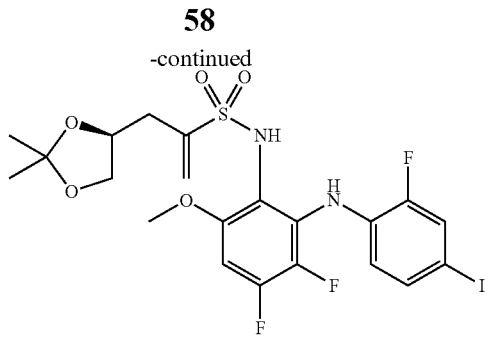

Step A: (S)-4-bromopent-4-ene-1,2-diol

A solution 9-bromo-9-borabicyclo[3.3.1]nonane (9-Br-BBN) in dichloromethane is added dropwise to a solution of (S)-1-(tert-butyldimethylsilyloxy)pent-4-yn-2-ol in dichloromethane at 0° C., and the mixture stirred at 0° C. for 4 hours. Glacial acetic acid is added and stirring continued at 0° C. for an additional 1 hour. Ethanolamine is added and the mixture allowed to warm to room temperature. The reaction is quenched by addition of an aqueous mixture of Na$_2$CO$_3$/Na$_2$S$_2$O$_3$ (1:1), extracted with ethyl acetate (3×), and the combined organic layers dried (MgSO$_4$) and concentrated under reduced pressure to afford (S)-4-bromopent-4-ene-1,2-diol.

Step B: (S)-4-(2-iodoallyl)-2,2-dimethyl-1,3-dioxolane 2,2 Dimethoxypropane (7.5 eq) and pyridinium p-toluenesulfonate (1 eq) are added to a solution of (R)-4-bromopent-4-ene-1,2-diol (5 eq) in dichloromethane and the mixture stirred at room temperature for 4 hours. Solvents are removed under reduced pressure and the crude product purified by flash chromatography (10% ethyl acetate/hexane, eluant).

Step C: (S)-3-(2,2-dimethyl-1,3-dioxolan-4-yl)prop-1-ene-2-sulfonyl chloride

A solution of tert-butyl lithium in hexane (1.7M, 2 eq) is added dropwise to a solution of (S)-4-(2-iodoallyl)-2,2-dimethyl-1,3-dioxolane (1 eq) in diethyl ether at −78° C., and the reaction stirred at −78° C. for 30 min. Sulfuryl dichloride (1 eq) is added, the mixture warmed to room temperature and the solvents removed under reduced pressure.

Step D: (S)—N-(3,4-difluoro-2-(2-fluoro-4-iodophenylamino)-6-methoxyphenyl)-3-(2,2-dimethyl-1,3-dioxolan-4-yl)prop-1-ene-2-sulfonamide

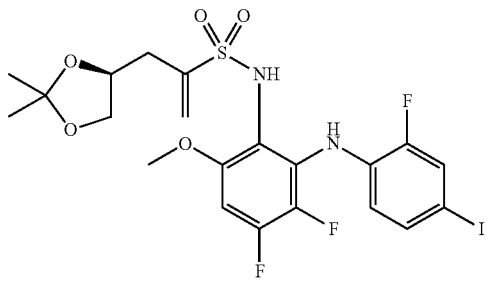 [SMILES: C=C(C[C@H]1COC(C)(C)O1)S(=O)(=O)Nc1c(OC)cc(F)c(F)c1Nc1ccc(I)cc1F]

(S)-3-(2,2-dimethyl-1,3-dioxolan-4-yl)prop-1-ene-2-sulfonyl chloride (1 eq) is dissolved in pyridine and 5,6-difluoro-$N^1$-(2-fluoro-4-iodophenyl)-3-methoxybenzene-1,2-diamine (1 eq) added. The solution is stirred at 100° C. for 2 hours and then partitioned with water and ethyl acetate. The organic layer is washed with brine, dried (MgSO$_4$), concentrated under reduced pressure and purified by flash column chromatography on silica (30% ethyl acetate/hexanes eluant).

Example 7

(R)-1-((2,2-dimethyl-1,3-dioxolan-4-yl)methyl)cyclopropane-1-sulfonyl chloride

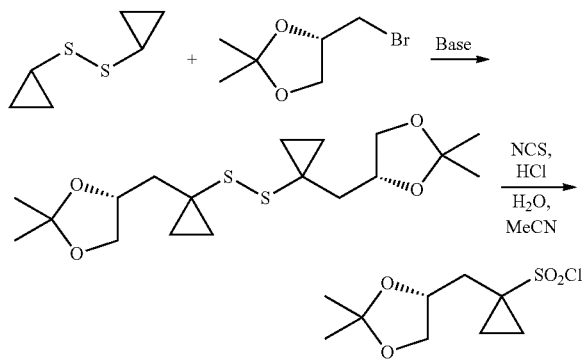

Step A: 1,2-Bis(1-(((R)-2,2-dimethyl-1,3-dioxolan-4-yl)methyl)cyclopropyl)disulfane

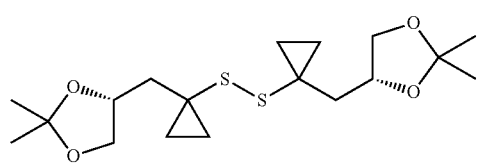

n-Butyl lithium (1.7 M in hexane, 1.2 eq) is added dropwise over 1 hour to a solution of 1,2-dicyclopropyldisulfane (1 eq) in THF (1.5 mL/mmol), at −20° C. (S)-4-(bromomethyl)-2,2-dimethyl-1,3-dioxolane (1.1 eq) is then added at −78° C. and stirring at −78° C. continued for an additional 4 hours. Saturated aqueous ammonium chloride solution is added and the mixture is extracted with ethyl acetate (3×). The combined organic extracts are dried (Na$_2$SO$_4$) and purified by flash chromatography (ethyl acetate in hexane eluant).

Step B: (R)-1-((2,2-dimethyl-1,3-dioxolan-4-yl)methyl)cyclopropane-1-sulfonyl chloride

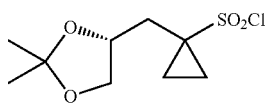

N-Chloro succinimide (NCS, 1 eq) is added to a mixture of 2 M HCl (0.6 mL/mmol) and acetonitrile (3.4 mL/mmol) and cooled to 10° C. A solution of 1,2-bis(1-(((R)-2,2-dimethyl-1,3-dioxolan-4-yl)methyl)cyclopropyl)disulfane (2.5 eq) in acetonitrile (0.25 ml/mmol) is added dropwise to the mixture, which is stirred below 20° C. for 20 minutes. Di-iso-propyl ether (15 ml/mmol) is added and the isolated organic layer washed with brine, dried (Na$_2$SO$_4$) concentrated under reduced pressure and the crude material purified by flash chromatography (ethyl acetate in hexane eluant). See Nishiguchi et al, *Synthesis*, 2006, 24, 4131-4134 for additional details.

Example 8

1,2-Bis(1-(((S)-2,2-dimethyl-1,3-dioxolan-4-yl)methyl)cyclopropyl)disulfane

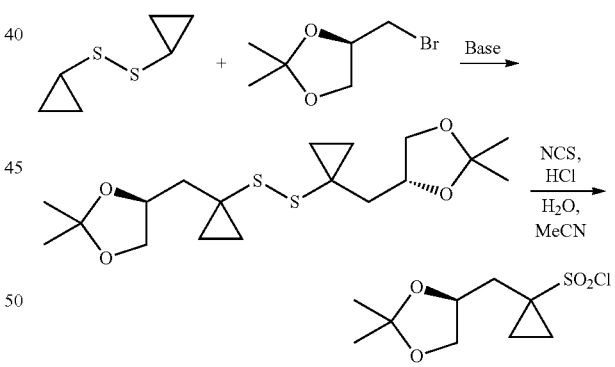

Step A: 1,2-Bis(1-(((S)-2,2-dimethyl-1,3-dioxolan-4-yl)methyl)cyclopropyl)disulfane

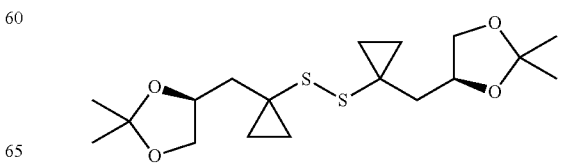

n-Butyl lithium (1.7 M in hexane, 1.2 eq) is added dropwise over 1 hour to a solution of 1,2-dicyclopropyldisulfane (1 eq) in THF (1.5 mL/mmol), at −20° C. (R)-4-(Bromomethyl)-2,2-dimethyl-1,3-dioxolane (1.1 eq) is then added at −78° C. and stiffing at −78° C. continued for an additional 4 hours. Saturated aqueous ammonium chloride solution is added and the mixture is extracted with ethyl acetate (3×). The combined organic extracts are dried (Na$_2$SO$_4$) and purified by flash chromatography (ethyl acetate in hexane eluant).

Step B: (S)-1-((2,2-dimethyl-1,3-dioxolan-4-yl)methyl)cyclopropane-1-sulfonyl chloride

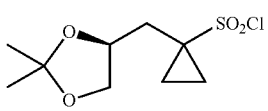

N-Chloro succinimide (NCS, 1 eq) is added to a mixture of 2 M HCl (0.6 mL/mmol) and acetonitrile (3.4 mL/mmol) and cooled to 10° C. A solution of 1,2-bis(1-(((S)-2,2-dimethyl-1,3-dioxolan-4-yl)methyl)cyclopropyl)disulfane (2.5 eq) in acetonitrile (0.25 ml/mmol) is added dropwise to the mixture, which is stirred below 20° C. for 20 minutes. Di-iso-propyl ether (15 ml/mmol) is added and the isolated organic layer washed with brine, dried (Na$_2$SO$_4$) concentrated under reduced pressure and the crude material purified by flash chromatography (ethyl acetate in hexane eluant). See Nishiguchi et al, *Synthesis*, 2006, 24, 4131-4134 for additional details.

Example 9

(R)-1-((2,2-Dimethyl-1,3-dioxolan-4-yl)methyl)cyclopropane-1-sulfonyl chloride

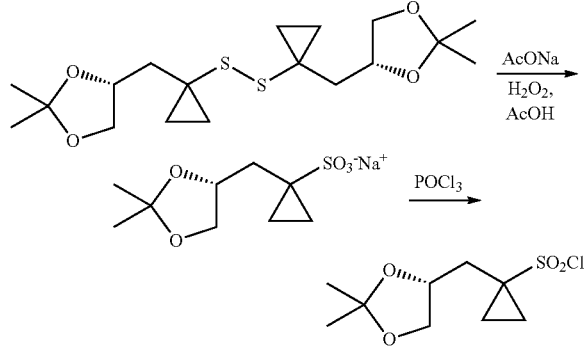

Step A: Sodium (R)-1-((2,2-dimethyl-1,3-dioxolan-4-yl)methyl)cyclopropane-1-sulfonate

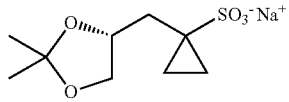

30% Hydrogen peroxide (9 eq) is added to a solution of 1,2-bis(1-(((R)-2,2-dimethyl-1,3-dioxolan-4-yl)methyl)cyclopropyl)disulfane (1 eq) and sodium acetate (2 eq) in acetic acid (5 mL/mmol). The solution is heated at 80° C. for 1 hour, cooled, concentrated under reduced pressure and the crude material purified by recrystallization. See Fernandez-Bolanos, et al, *Carbohydrate Research*, 1988, 173(1), 33-40, for additional details.

Step B: (R)-1-((2,2-Dimethyl-1,3-dioxolan-4-yl)methyl)cyclopropane-1-sulfonyl chloride

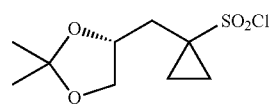

A solution of sodium (R)-1-((2,2-dimethyl-1,3-dioxolan-4-yl)methyl)cyclopropane-1-sulfonate (1 eq) and phosphoryl trichloride (POCl$_3$, 0.7 mL/mmol) is heated at 80° C. for 1 hour. The reaction mixture is cooled to room temperature, poured onto ice, stirred for 30 minutes and extracted with chloroform (2×). The combined organic extracts are dried (MgSO$_4$) and concentrated under reduced pressure.

Example 10

(S)-1-((2,2-Dimethyl-1,3-dioxolan-4-yl)methyl)cyclopropane-1-sulfonyl chloride

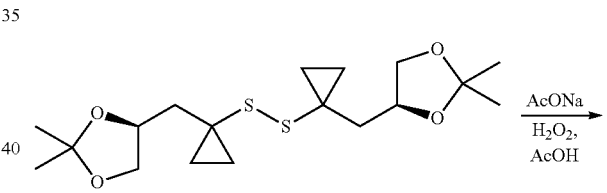

Step A: Sodium (S)-1-((2,2-dimethyl-1,3-dioxolan-4-yl)methyl)cyclopropane-1-sulfonate

30% Hydrogen peroxide (9 eq) is added to a solution of 1,2-bis(1-(((S)-2,2-dimethyl-1,3-dioxolan-4-yl)methyl)cyclopropyl)disulfane (1 eq) and sodium acetate (2 eq) in acetic acid (5 mL/mmol). The solution is heated at 80° C. for 1 hour, cooled, concentrated under reduced pressure and the crude material purified by recrystallization. See Fernandez-Bolanos, et al, *Carbohydrate Research,* 1988, 173(1), 33-40, for additional details.

Step B: (S)-1-((2,2-Dimethyl-1,3-dioxolan-4-yl)methyl)cyclopropane-1-sulfonyl chloride

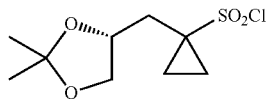

A solution of sodium (S)-1-((2,2-dimethyl-1,3-dioxolan-4-yl)methyl)cyclopropane-1-sulfonate (1 eq) and phosphoryl trichloride ($POCl_3$, 0.7 mL/mmol) is heated at 80° C. for 1 hour. The reaction mixture is cooled to room temperature, poured onto ice, stirred for 30 minutes and extracted with chloroform (2×). The combined organic extracts are dried ($MgSO_4$) and concentrated under reduced pressure.

Example 11

(R)-1-((2,2-Dimethyl-1,3-dioxolan-4-yl)methyl)cyclopropane-1-sulfonyl chloride

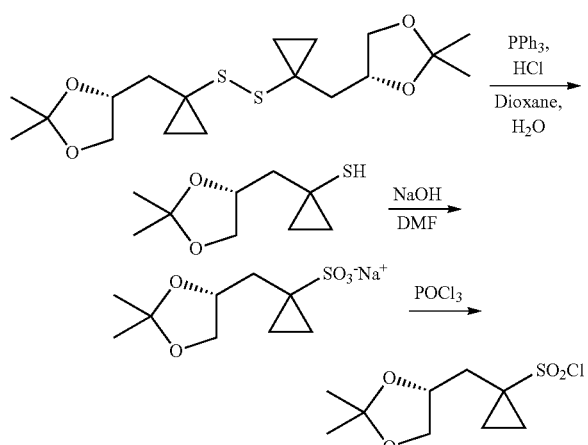

Step A: (R)-1-((2,2-Dimethyl-1,3-dioxolan-4-yl)methyl)cyclopropanethiol

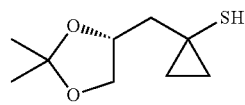

A solution of 1,2-bis(1-(((R)-2,2-dimethyl-1,3-dioxolan-4-yl)methyl)cyclopropyl)disulfane (1 eq) and triphenylphosphine in a mixture of dioxane and water (4/1) containing two drops of concentrated hydrochloric acid is stirred at 40° C. for 20 min and concentrated under reduced pressure. The crude material is purified by flash chromatography (ethyl acetate in hexane eluant). See Overman et al, *Synthesis,* 1974, 59-60 for additional details.

Step B: Sodium (R)-1-((2,2-dimethyl-1,3-dioxolan-4-yl)methyl)cyclopropane-1-sulfonate

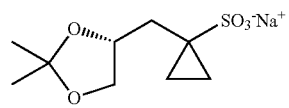

Sodium hydroxide (4 eq) is added to a solution of (R)-1-((2,2-dimethyl-1,3-dioxolan-4-yl)methyl)cyclopropanethiol (1 eq) in DMF (0.5 mL/mmol), and stirred at room temperature overnight and hydrolyzed. The mixture is extracted with ethyl acetate (3×), and the combined organic layers dried ($MgSO_4$), concentrated under reduced pressure and the crude material recrystallized.

Step C: (R)-1-((2,2-Dimethyl-1,3-dioxolan-4-yl)methyl)cyclopropane-1-sulfonyl chloride

A solution of sodium (R)-1-((2,2-dimethyl-1,3-dioxolan-4-yl)methyl)cyclopropane-1-sulfonate (1 eq) and phosphoryl trichloride ($POCl_3$, 0.7 mL/mmol) is heated at 80° C. for 1 hour. The reaction mixture is cooled to room temperature, poured onto ice, stirred for 30 minutes and extracted with chloroform (2×). The combined organic extracts are dried ($Mg5O_4$) and concentrated under reduced pressure.

Example 12

(S)-1-((2,2-Dimethyl-1,3-dioxolan-4-yl)methyl)cyclopropane-1-sulfonyl chloride

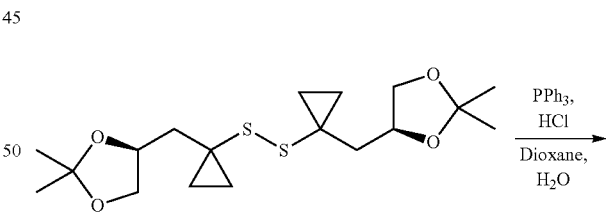

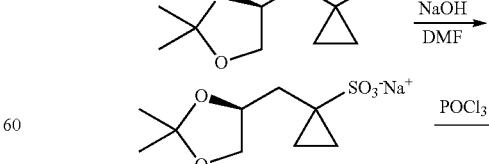

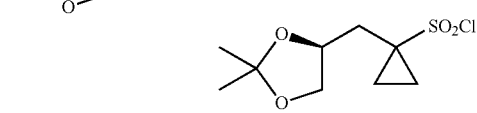

Step A: (S)-1-((2,2-Dimethyl-1,3-dioxolan-4-yl)methyl)cyclopropanethiol

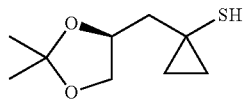

A solution of 1,2-bis(1-(((S)-2,2-dimethyl-1,3-dioxolan-4-yl)methyl)cyclopropyl)disulfane (1 eq) and triphenylphosphine in a mixture of dioxane and water (4/1) containing two drops of concentrated hydrochloric acid is stirred at 40° C. for 20 min and concentrated under reduced pressure. The crude material is purified by flash chromatography (ethyl acetate in hexane eluant). See Overman et al, *Synthesis*, 1974, 59-60 for additional details.

Step B: Sodium (S)-1-(2,2-dimethyl-1,3-dioxolan-4-yl)methyl)cyclopropane-1-sulfonate

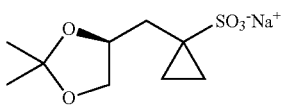

Sodium hydroxide (4 eq) is added to a solution of (S)-1-((2,2-dimethyl-1,3-dioxolan-4-yl)methyl)cyclopropanethiol (1 eq) in DMF (0.5 mL/mmol), and stirred at room temperature overnight and hydrolyzed. The mixture is extracted with ethyl acetate (3×), and the combined organic layers dried (MgSO$_4$), concentrated under reduced pressure and the crude material recrystallized.

Step C: (S)-1-((2,2-Dimethyl-1,3-dioxolan-4-yl)methyl)cyclopropane-1-sulfonyl chloride

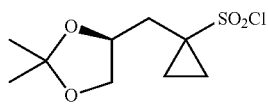

A solution of sodium (S)-1-((2,2-dimethyl-1,3-dioxolan-4-yl)methyl)cyclopropane-1-sulfonate (1 eq) and phosphoryl trichloride (POCl$_3$, 0.7 mL/mmol) is heated at 80° C. for 1 hour. The reaction mixture is cooled to room temperature, poured onto ice, stirred for 30 minutes and extracted with chloroform (2×). The combined organic extracts are dried (MgSO$_4$) and concentrated under reduced pressure.

Example 13

Figure 2:
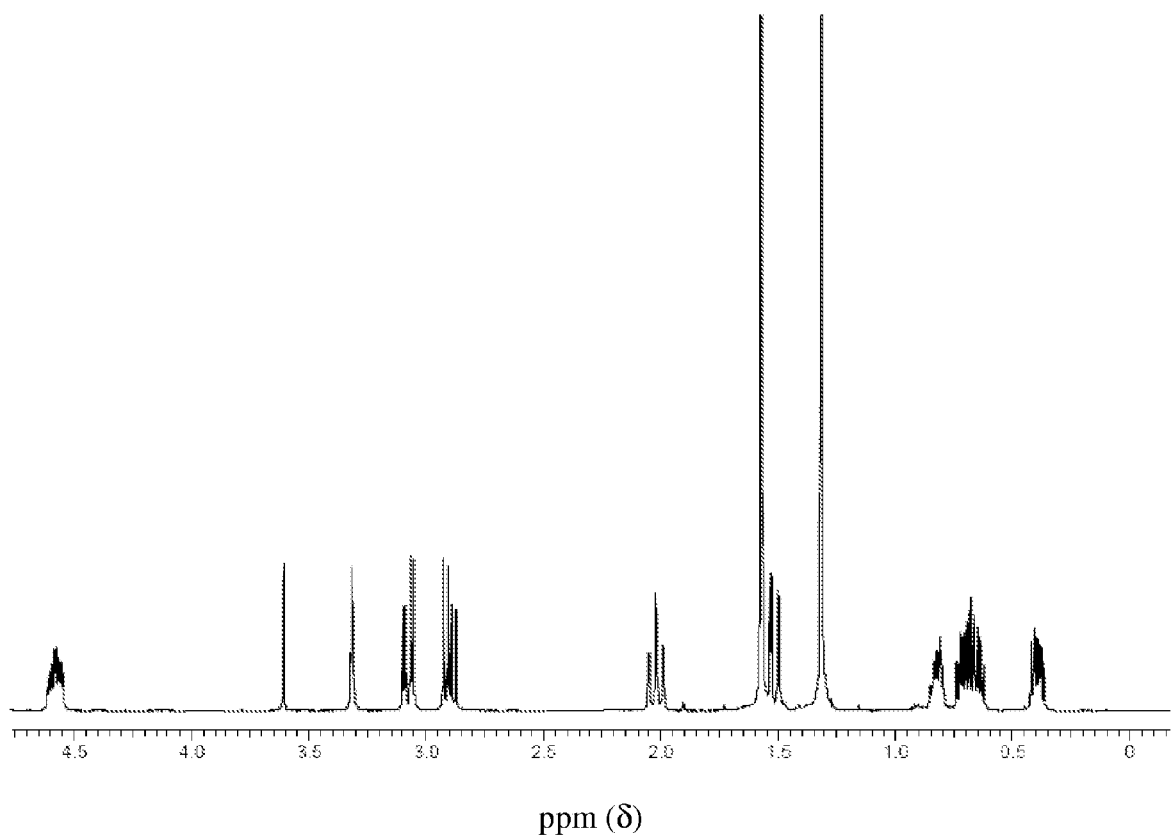
FIG. 2 represents the $^1$H NMR spectrum of sodium (S)-1-((2,2-dimethyl-1,3-dioxolan-4-yl)methyl)cyclopropane-1-sulfonate in CD$_3$OD.

FIG. 2 shows the $^1$H NMR spectrum of sodium (S)-1-((2,2-dimethyl-1,3-dioxolan-4-yl)methyl)cyclopropane-1-sulfonate in CD$_3$OD.

$^1$H NMR (400 MHz, CD$_3$OD) δ ppm 0.39 (ddd, J=9.85, 6.71, 5.27 Hz, 1H), 0.57-0.76 (m, 2H), 0.76-0.89 (m, 1H), 1.31 (s, 3H), 1.51 (dd, J=13.30, 2.76 Hz, 1H), 1.57 (s, 3H), 1.94-2.07 (m, 1H), 2.89 (dd, J=13.80, 8.03 Hz, 1H), 3.07 (dd, J=13.80, 4.27 Hz, 1H), 4.51-4.62 (m, 1H).

Example 14

Figure 3:
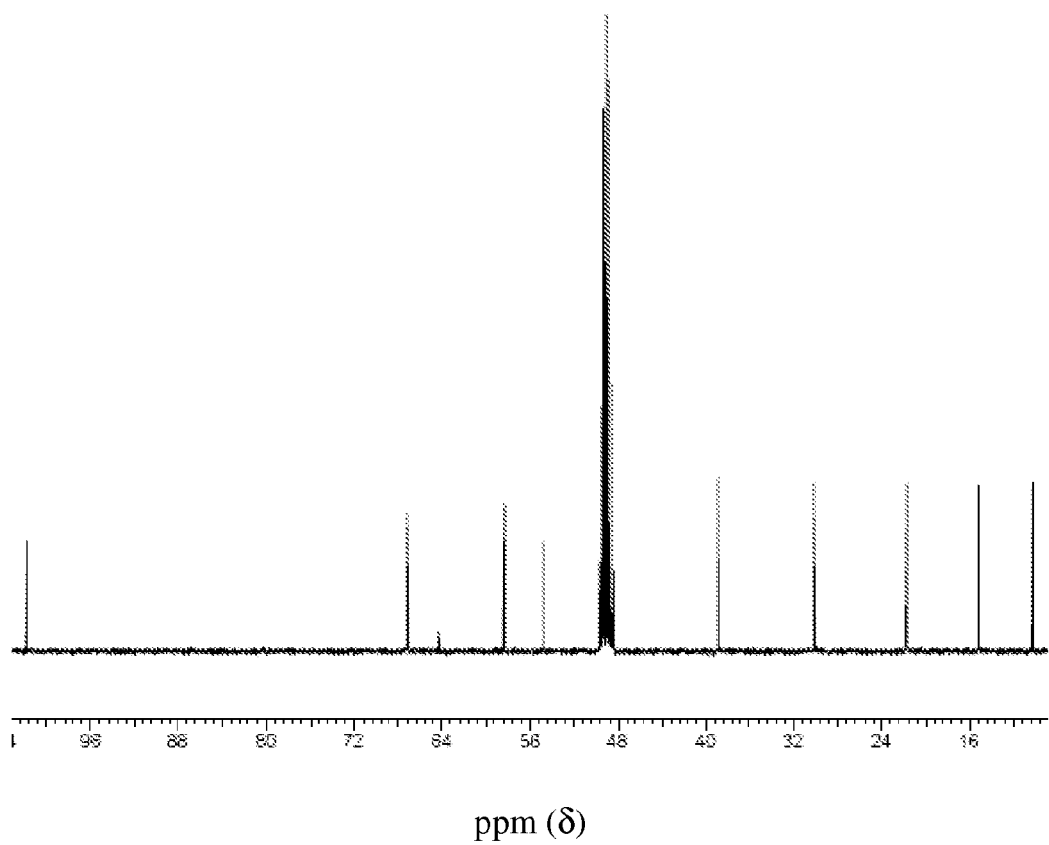
FIG. 3 represents the $^{13}$C NMR spectrum of sodium (S)-1-((2,2-dimethyl-1,3-dioxolan-4-yl)methyl)cyclopropane-1-sulfonate in CD$_3$OD.

FIG. 3 shows the $^{13}$C NMR spectrum of sodium (S)-1-((2,2-dimethyl-1,3-dioxolan-4-yl)methyl)cyclopropane-1-sulfonate in CD$_3$OD.

$^{13}$C NMR (METHANOL-d$_4$) δ ppm 10.30, 15.17, 21.75, 30.13, 38.88, 54.79, 58.37, 67.15, 101.78.

The entire disclosures of all applications, patents and publications, cited herein and of corresponding U.S. patent application Ser. No. 13/386,519, filed Jan. 23, 2012 are incorporated by reference herein.

What is claimed is:

1. A process for preparing (R)—N-(3,4-difluoro-2-(2-fluoro-4-iodophenylamino)-6-methoxyphenyl)-1-(2,3-dihydroxypropyl)cyclopropane-1-sulfonamide, comprising, contacting a compound of formula (I-a) with an acid, a base or a nucleophile; or exposing the compound of formula (I-a) to UV light:

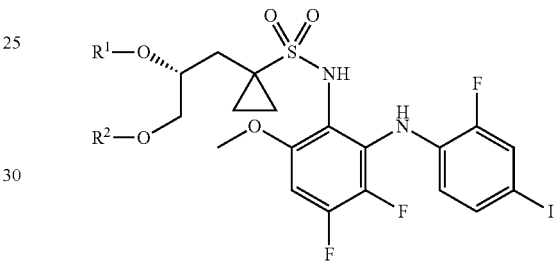

formula (I-a)

wherein
R$^1$ is H or an alcohol protecting group;
R$^2$ is H or an alcohol protecting group; or
R$^1$ and R$^2$ together with the carbon atoms to which they are attached form a cyclic 1,2-diol protecting group,
wherein R$^1$ and R$^2$ cannot both be H.

2. A process for preparing (S)—N-(3,4-difluoro-2-(2-fluoro-4-iodophenylamino)-6-methoxyphenyl)-1-(2,3-dihydroxypropyl)cyclopropane-1-sulfonamide, comprising, contacting a compound of formula (I-b) with an acid, a base or a nucleophile; or
exposing the compound of formula (I-b) to UV light:

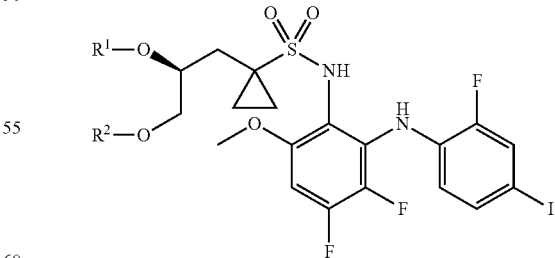

formula (I-b)

wherein
R$^1$ is H or an alcohol protecting group;
R$^2$ is H or an alcohol protecting group; or
R$^1$ and R$^2$ together with the carbon atoms to which they are attached form a cyclic 1,2-diol protecting group,
wherein R$^1$ and R$^2$ cannot both be H.

3. A process of claim 1, wherein $R^1$ and $R^2$ together with the carbon atoms to which they are attached form a cyclic 1,2-diol protecting group.

4. A process of claim 2, wherein $R^1$ and $R^2$ together with the carbon atoms to which they are attached form a cyclic 1,2-diol protecting group.

5. The process of claim 3, wherein the cyclic 1,2-diol protecting group is a 5-membered cyclic 1,2-diol protecting group.

6. The process of claim 4, wherein the cyclic 1,2-diol protecting group is a 5-membered cyclic 1,2-diol protecting group.

7. The process of claim 3, wherein the cyclic 1,2-diol protecting group is 2,2-dimethyl-1,3-dioxolan-4-yl.

8. The process of claim 4, wherein the cyclic 1,2-diol protecting group is 2,2-dimethyl-1,3-dioxolan-4-yl.

* * * * *